US012661525B2

(12) United States Patent
Hopkins et al.

(10) Patent No.: US 12,661,525 B2
(45) Date of Patent: Jun. 23, 2026

(54) SYSTEMS AND METHODS FOR TRANSCRANIAL LIGHT THERAPY

(71) Applicant: Neuro Therapy Solutions, LLC, San Clemente, CA (US)

(72) Inventors: Mitchell E. Hopkins, Fountain Valley, CA (US); Gilbert John Ballow, San Clemente, CA (US); Jeffrey Scott Andrews, Hood River, OR (US)

(73) Assignee: Neuro Therapy Solutions, LLC, San Clemente, CA (US)

( * ) Notice: Subject to any disclaimer, the term of this patent is extended or adjusted under 35 U.S.C. 154(b) by 742 days.

(21) Appl. No.: 17/458,004

(22) Filed: Aug. 26, 2021

(65) Prior Publication Data

US 2023/0066559 A1     Mar. 2, 2023

(51) Int. Cl.
*A61N 5/06*          (2006.01)
(52) U.S. Cl.
CPC .... *A61N 5/0622* (2013.01); *A61N 2005/0632* (2013.01); *A61N 2005/0648* (2013.01)
(58) Field of Classification Search
CPC .... A61N 2005/0632; A61N 2005/0633; A61N 2005/0648; A61N 5/0622
See application file for complete search history.

(56) References Cited

U.S. PATENT DOCUMENTS

2014/0231474 A1*   8/2014   Sugihara ............... G02B 7/002
                                                                         224/181

* cited by examiner

*Primary Examiner* — Alyssa M Alter
(74) *Attorney, Agent, or Firm* — Dax D. Anderson; Kirton McConkie

(57) ABSTRACT

Systems and methods for transcranial light therapy address the deficiencies inherent in previous light therapy devices. Improved adjustability of the location, placement, and directionality of the applied light, thereby improving efficiency of transcranial light delivery and facilitating customization of fitment of the light therapy devices to users of differently sized and differently shaped human heads and hair is provided. Improved mechanisms and methods for controlling light therapy application at each of a plurality of light application locations are also provided, such that light therapy treatments can be highly customized for each individual and/or therapy purpose. Simultaneous, sequential, or separate ocular visible light therapy is also available, thereby increasing the options for customized therapy modalities. The therapy devices are highly modular, permitting simplified repair and maintenance of device components upon component failure and allowing unnecessary device components to be removed from the device when not being used, thereby increasing user comfort.

11 Claims, 21 Drawing Sheets

1

SYSTEMS AND METHODS FOR TRANSCRANIAL LIGHT THERAPY

BACKGROUND OF THE INVENTION

1. Field of the Invention

The present invention relates to light therapy and more particularly to systems and methods for providing transcranial light therapy at multiple locations of the human head.

2. Background and Related Art

Transcranial light therapy has shown promising benefits for treatment of a variety of conditions. As a result, a number of devices have been created to provide transcranial light therapy. Such devices attempt to deliver light (often infrared or red light) transcranially at one or more locations of the scalp. Some such devices also deliver light intranasally via a nasal clip.

While such devices have provided some of the benefits of transcranial light therapy, these devices have failed to or struggle to provide all of the intended benefits of such therapy. Such devices typically have minimal adjustability and are unable to provide customized treatments. Instead, such devices provide treatment of limited effectiveness. Accordingly, improvements in transcranial light therapy devices and methods would be beneficial.

BRIEF SUMMARY OF THE INVENTION

Implementation of the invention provides systems and methods for transcranial light therapy that address the deficiencies inherent in previous light therapy devices. Implementations of the invention provide improved adjustability of the location, placement, and directionality of the applied light, thereby improving efficiency of transcranial light delivery and facilitating customization of fitment of the light therapy devices to users of differently sized and differently shaped human heads. Implementations of the invention further provide improved mechanisms and methods for controlling light therapy application at each of a plurality of light application locations, such that light therapy treatments can be highly customized for each individual and/or therapy purpose. Implementations of the invention further provide for simultaneous, sequential, or separate ocular visible light therapy, thereby increasing the options for customized therapy modalities. Implementations of the invention further provide for highly modular therapy devices, such that unnecessary device components can be removed from the device when not being used in a particular therapy plan, thereby increasing user comfort. The modularity of the therapy devices also permits for simplified repair and maintenance of device components upon component failure. Further advantages of implementations of the invention will become apparent through the appended description and drawings.

According to implementations of the invention, a light therapy device, includes a headpiece, a light arm having a proximal end and a distal end and a headpiece-light arm joint, wherein the headpiece-light arm joint is disposed proximate the proximal end of the light arm and wherein the headpiece-light arm joint connects the headpiece and the light arm in such a way that provides rotational and pivotal motion of the light arm relative to the headpiece. The light therapy device further includes a light pod, and a light arm-light pod joint, wherein the light arm-light pod joint is disposed proximate the distal end of the light arm and connects the light arm and the light pod in such a way that provides pivotal motion of the light pod relative to the light arm.

In some implementations, the headpiece is adapted to rest on a human head. In some implementations, the light arm is one of a plurality of light arms. In some implementations, the light arm is selectively connected to the light arm joint in such a way that provides sliding translational motion of the light arm relative to the headpiece. In some implementations, a pin slot joint selectively connects the light arm and the light arm joint to provide the sliding translational motion of the light arm relative to the headpiece.

In some implementations, the headpiece-light arm joint includes a ball and socket joint. In some implementations, the light arm-light pod joint includes a ball and socket joint providing at least pivotal motion of the light pod relative to the light arm. In some implementations, the light pod includes a plurality of light-emitting diodes ("LEDs"). In some implementations, the light pod includes three LEDs. In some implementations, the LEDs are each enclosed within a light tube having a bullet-shaped lens covering that provides direct scalp contact, and the light tubes are internally coated to target light delivery through the tip of each LED light tube or lens covering.

In some implementations, the device further includes a temple light support having a proximal end and a distal end, a temple light pod, a headpiece-temple light support joint, wherein the a headpiece-temple light support joint is disposed proximate the proximal end of the temple light support and connects the temple light support to the headpiece in such a way that provides hinged motion of the temple light support relative to the headpiece, and a temple light support-temple light pod joint, wherein the temple light support-temple light pod joint is disposed proximate the distal end of the temple light support and connects the temple light support to the temple light pod in such a way that provides pivotal motion of the temple light pod relative to the temple light support. In some implementations, the headpiece-temple light support joint includes a clip. In some implementations, the temple light support-light pod joint includes a ball and socket joint.

In some implementations, the device includes four light arms and four headpiece-light arm joints, wherein each of the four headpiece-light arm joints connects one of the four light arms to the headpiece. In some implementations, the device further includes two temple light supports and two headpiece-temple light support joints, wherein each of the two headpiece-temple light support joints connects one of the two temple light supports to the headpiece. In some implementations, the device further includes four light arm-light pod joints, two temple light support-light pod joints, and six light pods, wherein each of the four light arm-light pod joints connects one of four of the light pods to one of the four light arms, and wherein each of the two temple light support-light pod joints connects one of two of the light pods and each of the two temple light supports. In some implementations, the device further includes a flip-up visible light panel, wherein the visible light panel includes a light bar having a proximal end and a distal end, wherein the proximal end of the light bar is selectively and removably connected to a front of the headpiece, and a visible light panel-light bar joint, wherein the visible light panel-light bar joint is disposed at the distal end of the light bar and wherein the visible light panel-light bar joint connects the visible light panel and the light bar in such a way that provides hinged motion of the visible light panel relative to the light bar.

According to additional implementations, a light therapy device includes a headpiece, wherein the headpiece is adapted to rest on a human head, a plurality of light pods, wherein each of the plurality of lights pods is selectively and removably attached to the headpiece and wherein each light pod includes a housing and a plurality of LEDs disposed in the housing, and a means for independently controlling activation of each of the plurality of light pods.

In some implementations, the means for independently controlling activation of each of the plurality of light pods independently controls which among the plurality of light pods is activated for treatment, using a mechanism such as one or more of the light pods being removably mounted to the headpiece, one or more of the light pods being articulable such that the plurality of LEDs of such light pod or pods are selectively distanced from the human head in use, an electronic control individually controlling each of the plurality of light pods, or an electronic control individually controlling each of the plurality of LEDs.

In some implementations, the means for independently controlling activation of each of the plurality of light pods includes a control for independently controlling a wavelength at which each light pod operates, the wavelength being a wavelength such as approximately 810 nm or approximately 650 nm. In some implementations, the means for independently controlling activation of each of the plurality of light pods includes a control for independently switching the light pods on and off at a duty cycle between approximately 30% and approximately 70% and at a frequency such as approximately 10 Hz or approximately 40 Hz. In some implementations, the means for independently controlling activation of each of the plurality of light pods includes a control for independently controlling a power density at which the light pods operate, the power density being a power density such as approximately 25 mW/cm², approximately 40 mW/cm2, or approximately 100 mW/cm2. In some implementations, the means for independently controlling activation of each of the plurality of light pods includes a control for independently controlling a treatment duration for which the light pods operate, the duration being a duration such as approximately 5 minutes, approximately 20 minutes, approximately 30 minutes, or approximately 40 minutes.

In some implementations, the means for independently controlling activation of each of the plurality of light pods includes a control box, wherein the control box is operatively connected to the light pods by a connection such as a wired connection or a wireless connection. In some implementations, the device further includes a visible light panel, wherein the visible light panel includes a plurality of visible-light LEDs, a light bar having a proximal end and a distal end, wherein the proximal end of the light bar is selectively and removably connected to a front of the headpiece, and a visible light panel-light bar joint, wherein the visible light panel-light bar joint is disposed proximal the distal end of the light bar and wherein the visible light panel-light bar joint connects the visible light panel and the light bar in such a way that provides hinged motion of the visible light panel relative to the light bar. In some implementations the means for independently controlling activation of each of the plurality of light pods further includes a control for independently switching the plurality of visible-light LEDs disposed in the visible light panel on and off at one or more wavelengths between approximately 380 nm and approximately 750 nm.

According to further implementations of the invention, a light therapy device includes a headpiece having a front and a back, a light bar having a proximal end and a distal end, wherein the proximal end of the light bar is selectively and removably connected to the front of the headpiece, a visible light panel, and a visible light panel-light bar joint, wherein the visible light panel-light bar joint is disposed proximate the distal end of the light bar and wherein the visible light panel-light bar joint connects the visible light panel and the light bar in such a way that provides hinged motion of the visible light panel relative to the light bar.

In some implementations, the visible light panel includes a plurality of white LEDs that selectively switch on and off at a frequency of approximately 40 Hz and a duty cycle of between approximately 30% and approximately 70%. In some implementations, the device further includes a plurality of light arms each having a proximal end and a distal end and a plurality of headpiece-light arm joints, wherein each headpiece-light arm joint is disposed proximate the proximal end of one of the light arms and wherein the headpiece-light arm joint connects the headpiece and the respective light arm in such a way that provides rotational and pivotal motion of the respective light arm relative to the headpiece. In some implementations, the device further includes a plurality of light pods each connected to one of the light arms, wherein the plurality of light pods each include a plurality of LEDs and a plurality of light arm-light pod joints, wherein each light arm-light pod joint is disposed proximate one distal end of one light arm and connects the respective light arm and the respective light pod in such a way that provides pivotal motion of the respective light pod relative to the respective light arm. In some implementations, the device further includes a nasal clip adapted to be clipped inside a human nostril, wherein the nasal clip includes a light-emitting diode (LED) and selectively operates at a wavelength of approximately 810 nm. In some implementations, the device further includes a means for independently controlling activation of each of the visible light panel, the plurality of light pods, and the nasal clip.

BRIEF DESCRIPTION OF THE SEVERAL VIEWS OF THE DRAWINGS

The objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

DETAILED DESCRIPTION OF THE INVENTION

Figure 1:
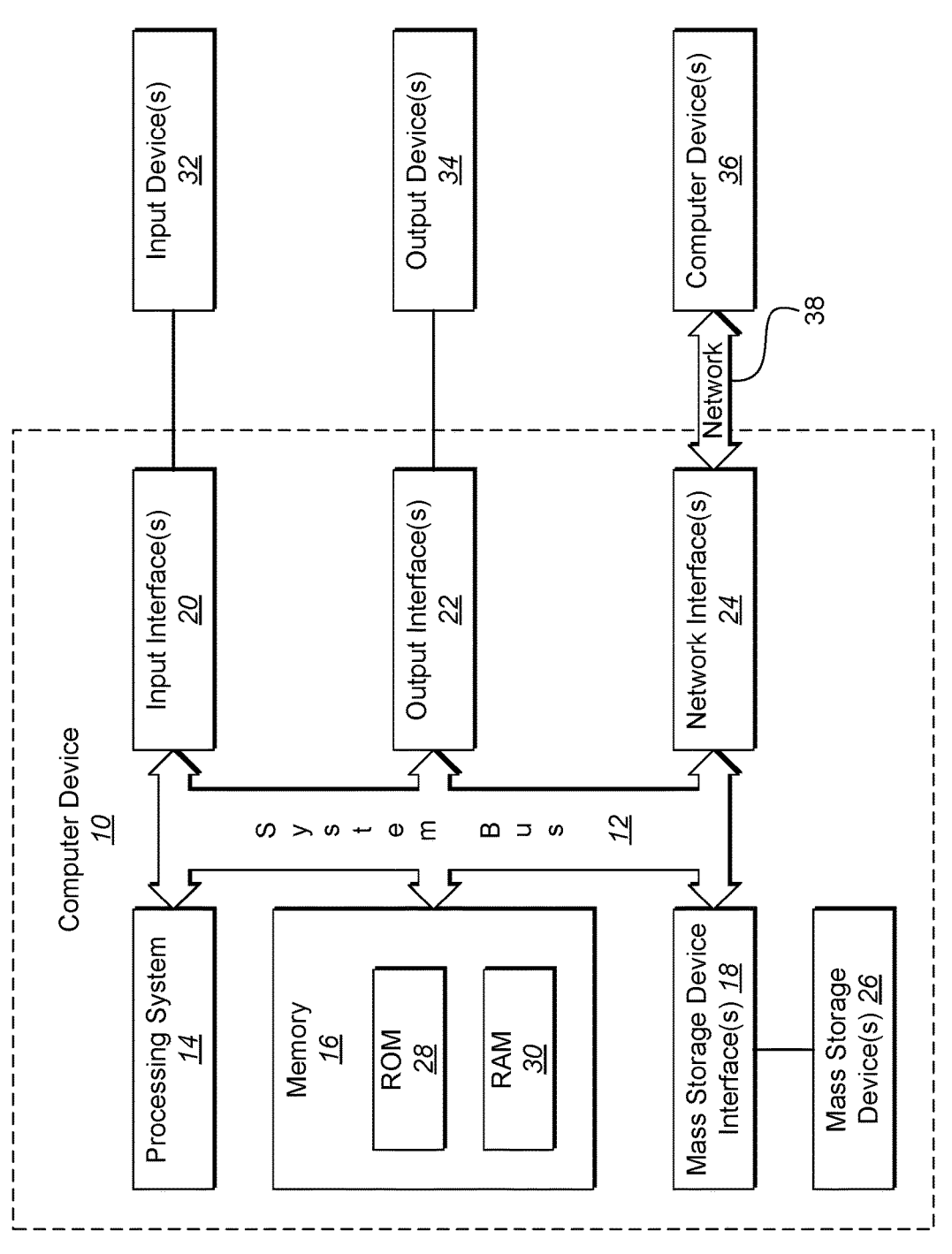
FIG. 1 shows a plan view of a representative computer system for use with embodiments of a light therapy device.

A description of embodiments of the present invention will now be given with reference to the Figures. It is expected that the present invention may take many other forms and shapes, hence the following disclosure is intended to be illustrative and not limiting, and the scope of the invention should be determined by reference to the appended claims.

Embodiments of the invention provide systems and methods for transcranial light therapy that address the deficiencies inherent in previous light therapy devices. Embodiments of the invention provide improved adjustability of the location, placement, and directionality of the applied light, thereby improving efficiency of transcranial light delivery and facilitating customization of fitment of the light therapy devices to users of differently sized and differently shaped human heads and/or heads with different hair coverage to maximize therapy effectiveness. Embodiments of the invention further provide improved mechanisms and methods for controlling light therapy application at each of a plurality of light application locations, such that light therapy treatments can be highly customized for each individual and/or therapy purpose. Embodiments of the invention further provide for simultaneous, sequential, or separate ocular visible light therapy, thereby increasing the options for customized therapy modalities. Embodiments of the invention further provide for highly modular therapy devices, such that unnecessary device components can be removed from the device when not being used in a particular therapy plan, thereby increasing user comfort. The modularity of the therapy devices also permits for simplified repair and maintenance of device components upon component failure. Further advantages of embodiments of the invention will become apparent through the description and drawings.

According to embodiments of the invention, a light therapy device, includes a headpiece, a light arm having a proximal end and a distal end and a headpiece-light arm joint, wherein the headpiece-light arm joint is disposed proximate the proximal end of the light arm and wherein the headpiece-light arm joint connects the headpiece and the light arm in such a way that provides rotational and pivotal motion of the light arm relative to the headpiece. The light therapy device further includes a light pod, and a light arm-light pod joint, wherein the light arm-light pod joint is disposed proximate the distal end of the light arm and connects the light arm and the light pod in such a way that provides pivotal motion of the light pod relative to the light arm. In some embodiments, the headpiece-light arm joint and the light arm-light pod joint collectively provide a dual gimbal design providing a wide range of motion to the light pod relative to the headpiece.

In some embodiments, the headpiece is adapted to rest on a human head. In some embodiments, the light arm is one of a plurality of light arms. In some embodiments, the light arm is selectively connected to the light arm joint in such a way that provides sliding translational motion of the light arm relative to the headpiece. In some embodiments, a pin slot joint selectively connects the light arm and the light arm joint to provide the sliding translational motion of the light arm relative to the headpiece.

In some embodiments, the headpiece-light arm joint includes a ball and socket joint. In some embodiments, the light arm-light pod joint includes a ball and socket joint providing at least pivotal motion of the light pod relative to the light arm. In some embodiments, the light pod includes a plurality of light-emitting diodes ("LEDs"). In some embodiments, the light pod includes three LEDs. In some embodiments, the LEDs are each enclosed within a light tube having a bullet-shaped lens covering that provides direct scalp contact, and the light tubes are internally coated to reflect the LED light to target light delivery through the tip of each LED light tube or lens covering.

In some embodiments, the device further includes a temple light support having a proximal end and a distal end, a temple light pod, a headpiece-temple light support joint, wherein the a headpiece-temple light support joint is disposed proximate the proximal end of the temple light support and connects the temple light support to the headpiece in such a way that provides hinged motion of the temple light support relative to the headpiece, and a temple light support-temple light pod joint, wherein the temple light support-temple light pod joint is disposed proximate the distal end of the temple light support and connects the temple light support to the temple light pod in such a way that provides pivotal motion of the temple light pod relative to the temple light support. In some embodiments, the headpiece-temple light support joint includes a clip. In some embodiments, the temple light support-light pod joint includes a ball and socket joint.

In some embodiments, the device includes four light arms and four headpiece-light arm joints, wherein each of the four headpiece-light arm joints connects one of the four light arms to the headpiece. In some embodiments, the device further includes two temple light supports and two headpiece-temple light support joints, wherein each of the two headpiece-temple light support joints connects one of the two temple light supports to the headpiece. In some embodiments, the device further includes four light arm-light pod joints, two temple light support-light pod joints, and six light pods, wherein each of the four light arm-light pod joints connects one of four of the light pods to one of the four light arms, and wherein each of the two temple light support-light pod joints connects one of two of the light pods and each of the two temple light supports. In some embodiments, the device further includes a flip-up visible light panel, wherein the visible light panel includes a light bar having a proximal end and a distal end, wherein the proximal end of the light bar is selectively and removably connected to a front of the headpiece, and a visible light panel-light bar joint, wherein the visible light panel-light bar joint is disposed at the distal end of the light bar and wherein the visible light panel-light bar joint connects the visible light panel and the light bar in such a way that provides hinged motion of the visible light panel relative to the light bar.

According to additional embodiments, a light therapy device includes a headpiece, wherein the headpiece is adapted to rest on a human head, a plurality of light pods, wherein each of the plurality of lights pods is selectively and removably attached to the headpiece and wherein each light pod includes a housing and a plurality of LEDs disposed in the housing, and a means for independently controlling activation of each of the plurality of light pods.

In some embodiments, the means for independently controlling activation of each of the plurality of light pods independently controls which among the plurality of light pods is activated for treatment, using a mechanism such as one or more of the light pods being removably mounted to the headpiece, one or more of the light pods being articulable such that the plurality of LEDs of such light pod or pods are selectively distanced from the human head in use, an electronic control individually controlling each of the plurality of light pods, or an electronic control individually controlling each of the plurality of LEDs.

In some embodiments, the means for independently controlling activation of each of the plurality of light pods includes a control for independently controlling a wavelength at which each light pod operates, the wavelength being a wavelength such as approximately 810 nm or approximately 650 nm. In some embodiments, the means for independently controlling activation of each of the plurality of light pods includes a control for independently switching the light pods on and off at a duty cycle between approximately 30% and approximately 70% and at a frequency such as approximately 10 Hz or approximately 40 Hz. In some embodiments, the means for independently controlling activation of each of the plurality of light pods includes a control for independently controlling a power density at which the light pods operate, the power density being a power density such as approximately 25 mW/cm2, approximately 40 mW/cm2, or approximately 100 mW/cm2. In some embodiments, the means for independently controlling activation of each of the plurality of light pods includes a control for independently controlling a treatment duration for which the light pods operate, the duration being a duration such as approximately 5 minutes, approximately 20 minutes, approximately 30 minutes, or approximately 40 minutes.

In some embodiments, the means for independently controlling activation of each of the plurality of light pods includes a control box, wherein the control box is operatively connected to the light pods by a connection such as a wired connection or a wireless connection. In some embodiments, the device further includes a visible light panel, wherein the visible light panel includes a plurality of visible-light LEDs, a light bar having a proximal end and a distal end, wherein the proximal end of the light bar is selectively and removably connected to a front of the headpiece, and a visible light panel-light bar joint, wherein the visible light panel-light bar joint is disposed proximal the distal end of the light bar and wherein the visible light panel-light bar joint connects the visible light panel and the light bar in such a way that provides hinged motion of the visible light panel relative to the light bar. In some embodiments the means for independently controlling activation of each of the plurality of light pods further includes a control for independently switching the plurality of visible-light LEDs disposed in the visible light panel on and off at one or more wavelengths between approximately 380 nm and approximately 750 nm.

According to further embodiments of the invention, a light therapy device includes a headpiece having a front and a back, a light bar having a proximal end and a distal end, wherein the proximal end of the light bar is selectively and removably connected to the front of the headpiece, a visible light panel, and a visible light panel-light bar joint, wherein the visible light panel-light bar joint is disposed proximate the distal end of the light bar and wherein the visible light panel-light bar joint connects the visible light panel and the light bar in such a way that provides hinged motion of the visible light panel relative to the light bar.

In some embodiments, the visible light panel includes a plurality of white LEDs that selectively switch on and off at a frequency of approximately 40 Hz and a duty cycle of between approximately 30% and approximately 70%. In some embodiments, the device further includes a plurality of light arms each having a proximal end and a distal end and a plurality of headpiece-light arm joints, wherein each headpiece-light arm joint is disposed proximate the proximal end of one of the light arms and wherein the headpiece-light arm joint connects the headpiece and the respective light arm in such a way that provides rotational and pivotal motion of the respective light arm relative to the headpiece. In some embodiments, the device further includes a plurality of light pods each connected to one of the light arms, wherein the plurality of light pods each include a plurality of LEDs and a plurality of light arm-light pod joints, wherein each light arm-light pod joint is disposed proximate one distal end of one light arm and connects the respective light arm and the respective light pod in such a way that provides pivotal motion of the respective light pod relative to the respective light arm. In some embodiments, the device further includes a nasal clip adapted to be clipped inside a human nostril, wherein the nasal clip includes a light-emitting diode (LED) and selectively operates at a wavelength of approximately 810 nm. In some embodiments, the device further includes a means for independently controlling activation of each of the visible light panel, the plurality of light pods, and the nasal clip.

In some embodiments, a means for independently controlling activation of features of the light therapy device includes a control box operatively connected (e.g., using a wired or wireless connection) to the light-emitting devices of the light therapy device. In such embodiments, the control box includes structure and/or logic providing features as discussed herein. Such structure and/or logic includes, in various embodiments, driving circuitry, timers, switches, buttons, power circuitry, logic circuitry, programmable circuitry/logic, and the like. As the various specific structure and/or logic that may be used to implement embodiments of the control box are myriad and will generally be well understood and recognized by one of ordinary skill in the art, specific examples of certain embodiments are only described in general terms.

In other embodiments, a means for independently controlling activation of features of the light therapy device includes a general purpose or special purpose computing device operatively connected to the light-emitting devices of the light therapy device. Accordingly, FIG. 1 and the corresponding discussion are intended to provide a general description of a suitable operating environment in which certain embodiments of the invention may be implemented. One skilled in the art will appreciate that embodiments of the invention may be practiced by one or more computing devices and in a variety of system configurations, including in a networked configuration. However, while the methods and processes of the present invention have proven to be particularly useful in association with a system comprising a general purpose computer, embodiments of the present invention include utilization of the methods and processes in a variety of environments, including embedded systems with general-purpose processing units, digital/media signal processors (DSP/MSP), application-specific integrated circuits (ASIC), stand-alone electronic devices, and other such electronic or computing environments.

Embodiments of the present invention embrace one or more computer-readable media, wherein each medium may be configured to include or includes thereon data or computer-executable instructions for manipulating data. The computer-executable instructions include data structures, objects, programs, routines, or other program modules that may be accessed by a processing system, such as one associated with a general-purpose computer capable of performing various different functions or one associated with a special-purpose computer capable of performing a limited number of functions. Computer-executable instructions cause the processing system to perform a particular function or group of functions and are examples of program code means for implementing steps for methods disclosed herein. Furthermore, a particular sequence of the executable instructions provides an example of corresponding acts that may be used to implement such steps. Examples of computer-readable media include random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM") and its successors, or any other device or component that is capable of providing data or executable instructions that may be accessed by a processing system. While embodiments of the invention embrace the use of all types of computer-readable media, certain embodiments as recited in the claims may be limited to the use of tangible, non-transitory computer-readable media, and the phrases "tangible computer-readable medium" and "non-transitory computer-readable medium" (or plural variations) used herein are intended to exclude transitory propagating signals per se.

With reference to FIG. 1, a representative system for implementing embodiments of the invention includes computer device 10, which may be a general-purpose or special-purpose computer or any of a variety of consumer electronic devices. For example, computer device 10 may be a personal computer, a notebook or laptop computer, a netbook, a personal digital assistant ("PDA") or other hand-held device, a smart phone, a tablet computer, a workstation, a minicomputer, a mainframe, a supercomputer, a multi-processor system, a network computer, a processor-based consumer electronic device, a computer device integrated into another device or vehicle, or the like.

Computer device 10 includes system bus 12, which may be configured to connect various components thereof and enables data to be exchanged between two or more components. System bus 12 may include one of a variety of bus structures including a memory bus or memory controller, a peripheral bus, or a local bus that uses any of a variety of bus architectures. Typical components connected by system bus 12 include processing system 14 and memory 16. Other components may include one or more mass storage device interfaces 18, input interfaces 20, output interfaces 22, and/or network interfaces 24, each of which will be discussed below.

Processing system 14 includes one or more processors, such as a central processor and optionally one or more other processors designed to perform a particular function or task. It is typically processing system 14 that executes the instructions provided on computer-readable media, such as on memory 16, a solid state drive, a removable solid state drive, a magnetic hard disk, a removable magnetic disk, a magnetic cassette, an optical disk, or from a communication connection, which may also be viewed as a computer-readable medium.

Memory 16 includes one or more computer-readable media that may be configured to include or includes thereon data or instructions for manipulating data, and may be accessed by processing system 14 through system bus 12. Memory 16 may include, for example, ROM 28, used to permanently store information, and/or RAM 30, used to temporarily store information. ROM 28 may include a basic input/output system ("BIOS") having one or more routines that are used to establish communication, such as during start-up of computer device 10. RAM 30 may include one or more program modules, such as one or more operating systems, application programs, and/or program data.

One or more mass storage device interfaces 18 may be used to connect one or more mass storage devices 26 to system bus 12. The mass storage devices 26 may be incorporated into or may be peripheral to computer device 10 and allow computer device 10 to retain large amounts of data. Optionally, one or more of the mass storage devices 26 may be removable from computer device 10. Examples of mass storage devices include solid state drives, hard disk drives, magnetic disk drives, tape drives and optical disk drives. A mass storage device 26 may read from and/or write to solid state memory, a magnetic hard disk, a removable magnetic disk, a magnetic cassette, an optical disk, or another computer-readable medium. Mass storage devices 26 and their corresponding computer-readable media provide nonvolatile storage of data and/or executable instructions that may include one or more program modules such as an operating system, one or more application programs, other program modules, or program data. Such executable instructions are examples of program code means for implementing steps for methods disclosed herein.

One or more input interfaces 20 may be employed to enable a user to enter data and/or instructions to computer device 10 through one or more corresponding input devices 32. Examples of such input devices 32 include a keyboard and alternate input devices, such as a mouse, trackball, light pen, stylus, or other pointing device, a microphone, a joystick, a game pad, a satellite dish, a scanner, a camcorder, a digital camera, and the like. Similarly, examples of input interfaces 20 that may be used to connect the input devices 32 to the system bus 12 include a serial port, a parallel port, a game port, a universal serial bus ("USB"), an integrated circuit, a firewire (IEEE 1394), or another interface. For example, in some embodiments, input interface 20 includes an application specific integrated circuit (ASIC) that is designed for a particular application. In a further embodiment, the ASIC is embedded and connects existing circuit building blocks.

One or more output interfaces 22 may be employed to connect one or more corresponding output devices 34 to system bus 12. Examples of output devices include a monitor or display screen, a speaker, a printer, a multi-functional peripheral, and the like. In some embodiments, one output device 34 is a light-therapy device. A particular output device 34 may be integrated with or peripheral to computer device 10. Examples of output interfaces include a video adapter, an audio adapter, a parallel port, and the like.

One or more network interfaces 24 enable computer device 10 to exchange information with one or more other local or remote computer devices, illustrated as computer devices 36, via a network 38 that may include hardwired and/or wireless links. Examples of network interfaces include a network adapter for connection to a local area network ("LAN") or a modem, wireless link, or other adapter for connection to a wide area network ("WAN"), such as the Internet. The network interface 24 may be incorporated with or peripheral to computer device 10. In a networked system, accessible program modules or portions thereof may be stored in a remote memory storage device. Furthermore, in a networked system, computer device 10 may participate in a distributed computing environment, where functions or tasks are performed by a plurality of networked computer devices.

Thus, while those skilled in the art will appreciate that embodiments of the present invention may be practiced in a variety of different environments with many types of system configurations, embodiments may be used with a networked system configuration. Other embodiments of the present invention include local, networked, or peer-to-peer environments where one or more computer devices may be connected to one or more local or remote peripheral devices. Moreover, embodiments in accordance with the present invention also embrace a single electronic consumer device, wireless networked environments, and/or wide area networked environments, such as the Internet. Similarly, embodiments of the invention embrace cloud-based architectures where one or more computer functions are performed by remote computer systems and devices at the request of a local computer device.

Figure 2:
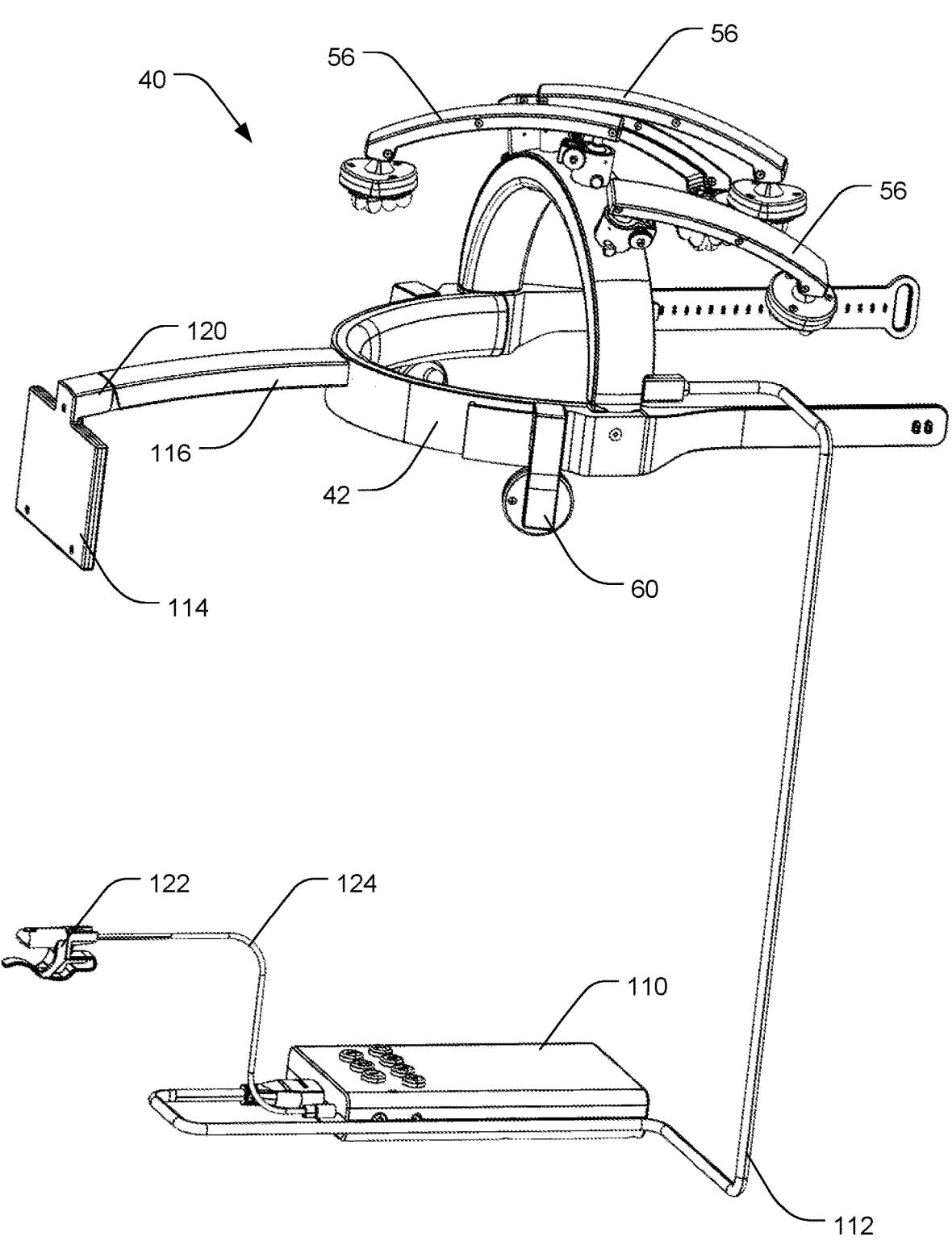
FIG. 2 shows a side perspective view of an embodiment of a light therapy device.
Figure 3:
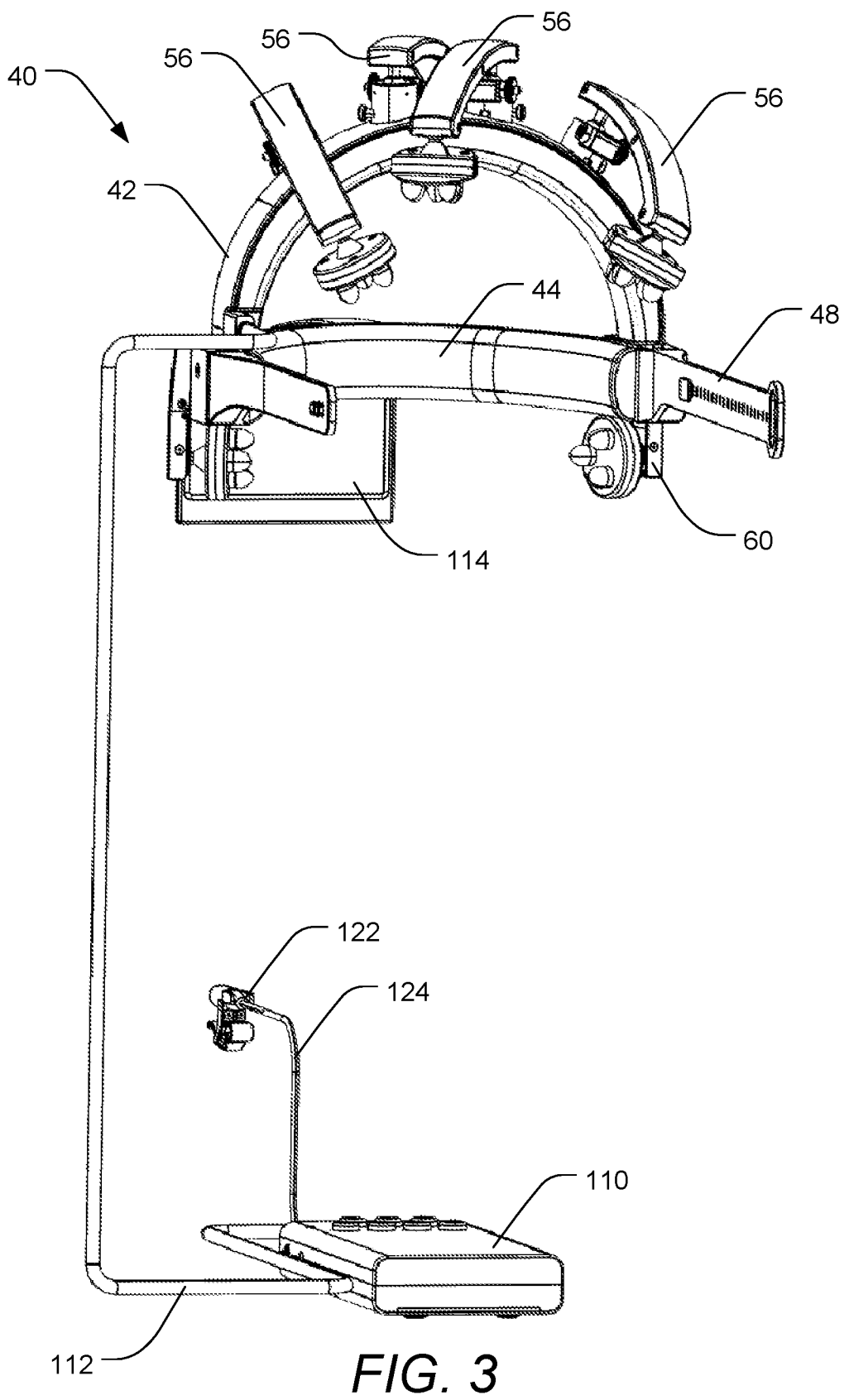
FIG. 3 shows a rear perspective view of the light therapy device of FIG. 2.
Figure 4:
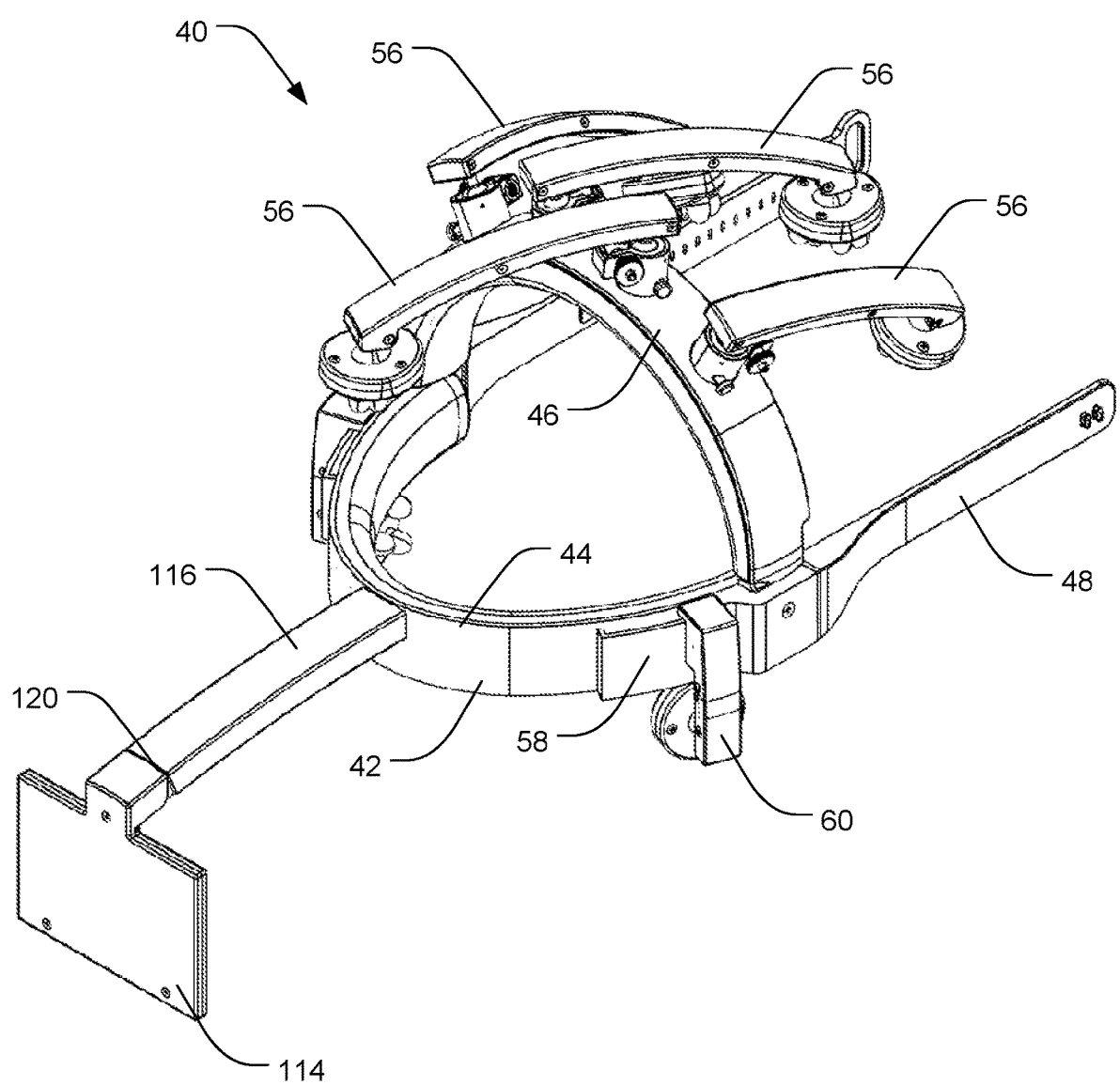
FIG. 4 shows a perspective view of a light therapy device without an attached wired controller.
Figure 5:
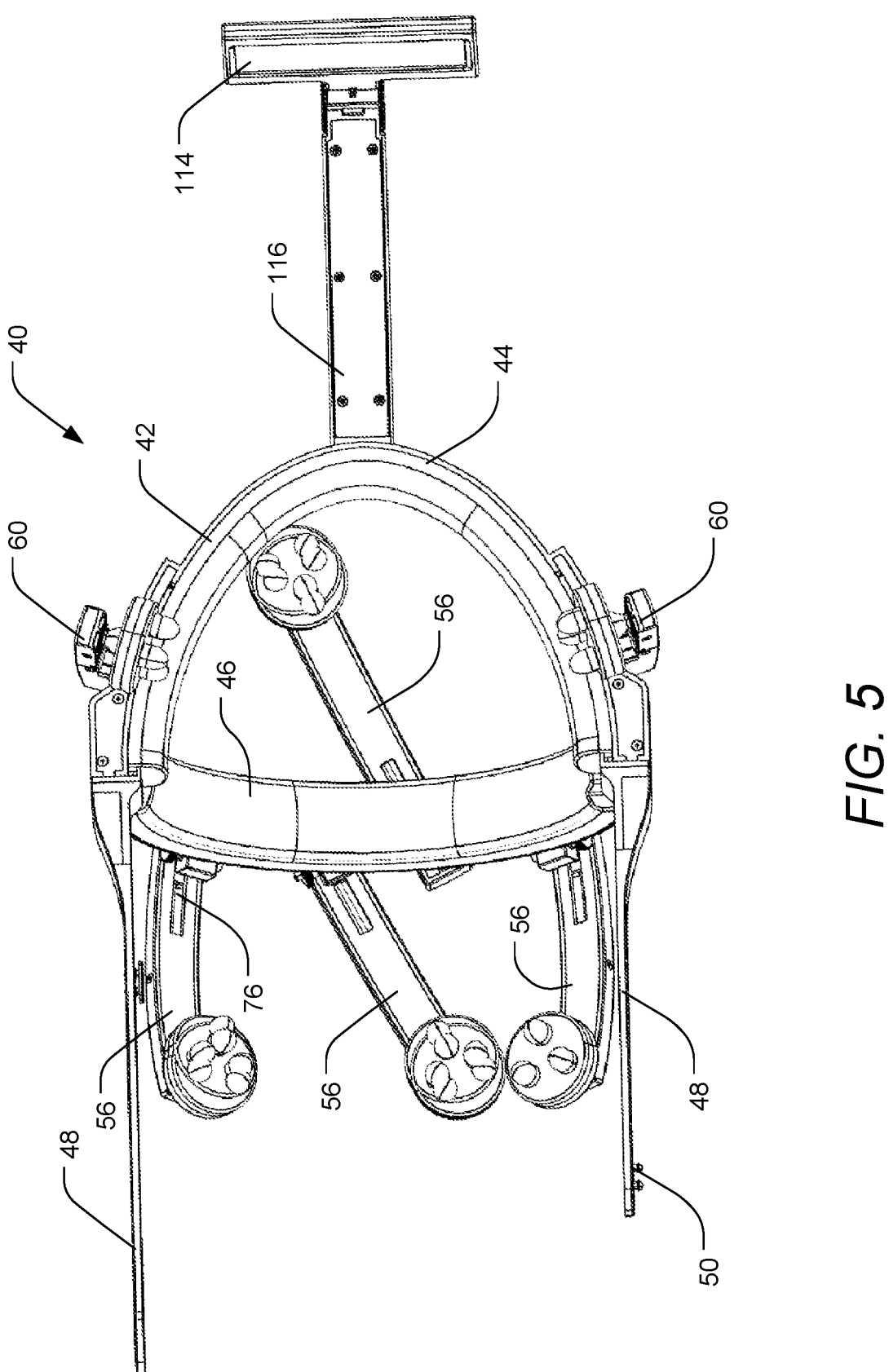
FIG. 5 shows a bottom view of the light therapy device without an attached control box.
Figure 6:
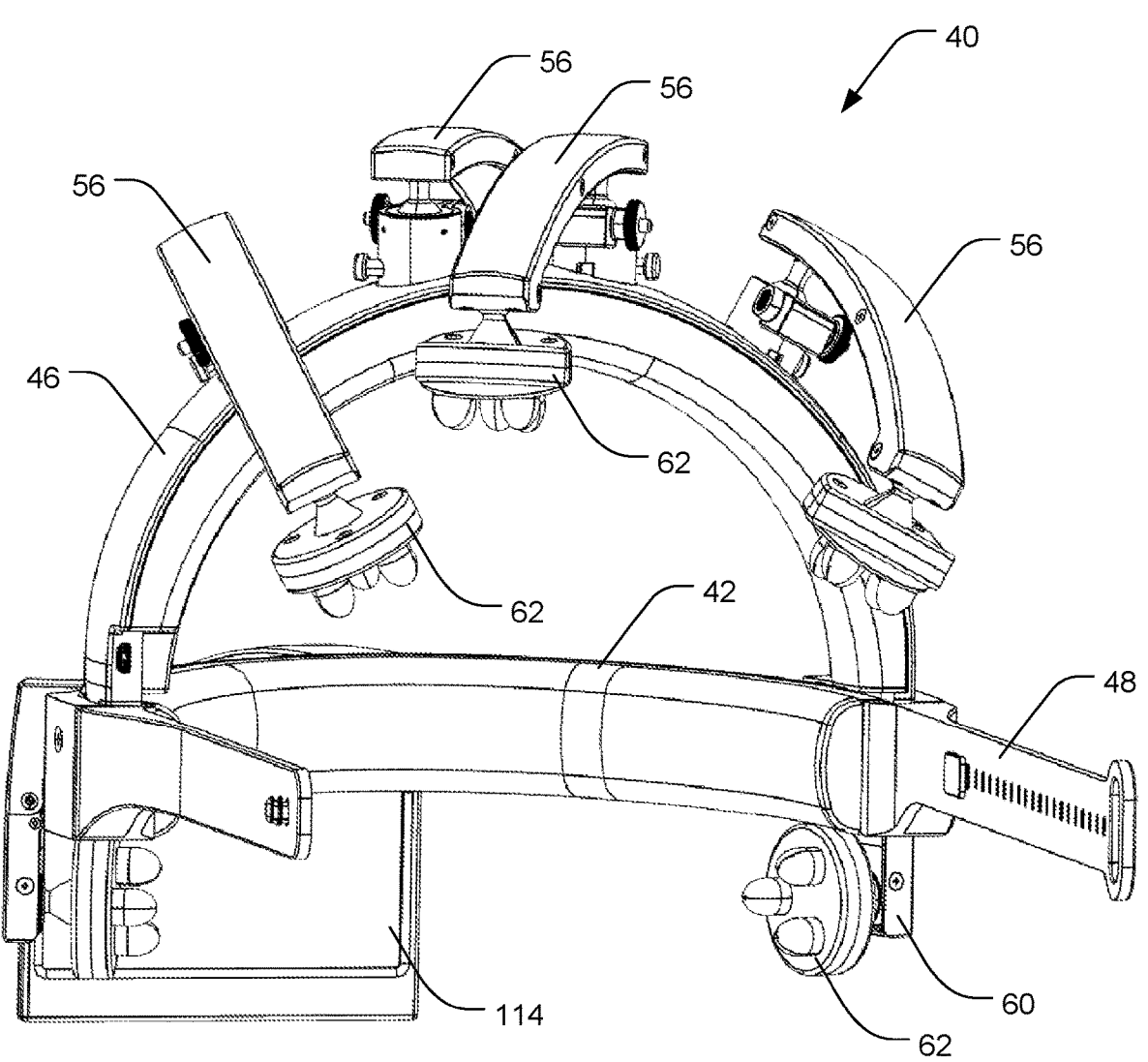
FIG. 6 shows a rear perspective view of the light therapy device without an attached control mechanism.

FIGS. 2 and 3 provide perspective views of one embodiment of a light therapy device 40 in accordance with embodiments of the invention. The light therapy device 40 includes a headpiece 42 adapted to rest on, fitted to, or gently secured to a human head for transcranial light therapy treatment. The headpiece 42 is shown in more detail in FIG. 12 and includes a forehead element 44 that extends forward from a central over-the-top element 46 so as to be adapted to generally encompass a wearer's forehead. The central over-the-top element 46 extends upward from each side of the forehead element 44 so as to be adapted to generally pass over a top of the wearer's head. One or more strap elements 48 extend generally rearward from the locations where the forehead element 44 and the central over-the-top element 46 join.

In the illustrated embodiment of the headpiece 42, the strap elements 48 are flexible and include one or more sizing elements, such as one or more sizing pins 50 in one of the strap elements 48 and a plurality of sizing holes 52 adapted to receive the sizing pins 50 and located in the other strap element 48. The sizing elements of the strap elements 48 allow the headpiece to be sized to comfortably but securely fit and rest on or be secured to the wearer's head. Inner portions of the forehead element 44, the central over-the-top element 46, and/or the strap elements 48 of some embodiments are provided with cushioning to aid in fit and/or comfort in wearing the headpiece 42 during treatment. If the light therapy device 40 is to be used for only one user, the strap elements 48 may be sized once and left in place indefinitely (with the headpiece 42 being lifted off of the head after treatment or placed on the head before treatment), or if the light therapy device 40 is to be used for multiple users, the strap elements 48 may be adjusted in size between users.

One or more of the forehead element 44, the central over-the-top element 46, and the strap elements 48 are at least partially unitarily formed in some embodiments (e.g., by a molding or casting process). In some embodiments, one or more of the forehead element 44, the central over-the-top element 46, and the strap elements 48 are separately formed and are then reversibly (in some embodiments) or more-or-less permanently (in other embodiments) attached to the other elements of the headpiece 42. Accordingly, embodiments of the headpiece are not limited to any strict form or method of formation or assembly while still falling within the scope of embodiments of the light therapy device 40.

Figure 12:
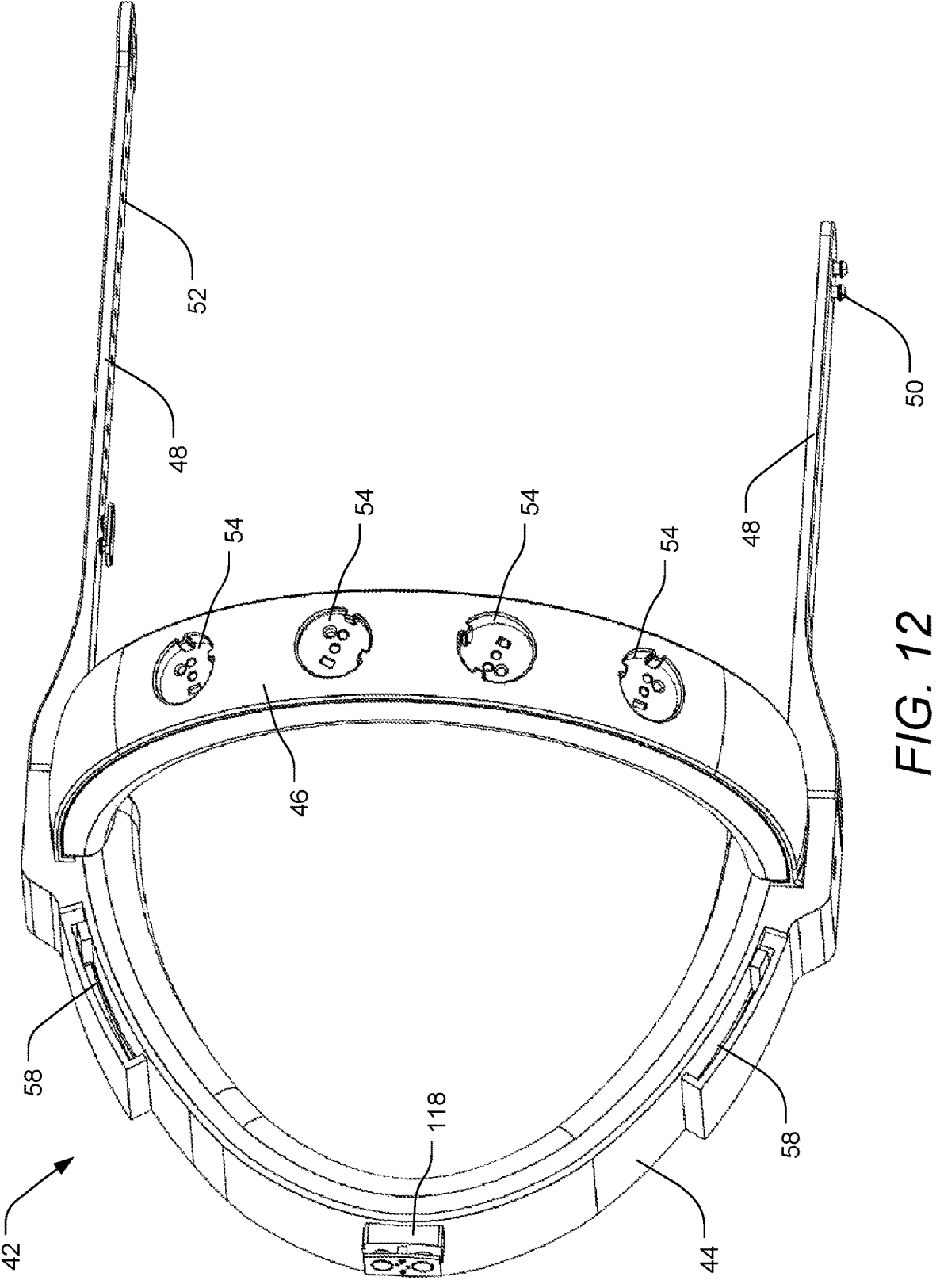
FIG. 12 shows a top perspective view of a headpiece for a light therapy device.

In the illustrated embodiment of the headpiece 42 shown in FIG. 12, it may be noted that the area of the headpiece between the central over-the-top element 46 and the forehead element 44 and between the central over-the-top element 46 and the strap elements 48 is left open or devoid of headpiece structure. This construction allows for variable placement of light delivery elements of the light therapy device 40 in a wide range of areas, as will be described in more detail subsequently. In other embodiments, however, more structure of the headpiece 42 may be present in the voids illustrated in FIG. 12, for aesthetic or functional reasons. As one example, a decorative cloth covering may extend between one or more of the forehead element 44, the central over-the-top element 46 and the strap elements 48 (while also extending over any light-delivery elements of the light therapy device 40 so as not to interfere with delivery of light to the wearer's scalp). Accordingly, embodiments of the headpiece 42 are not limited to the specific form illustrated in the Figures.

Figure 13:
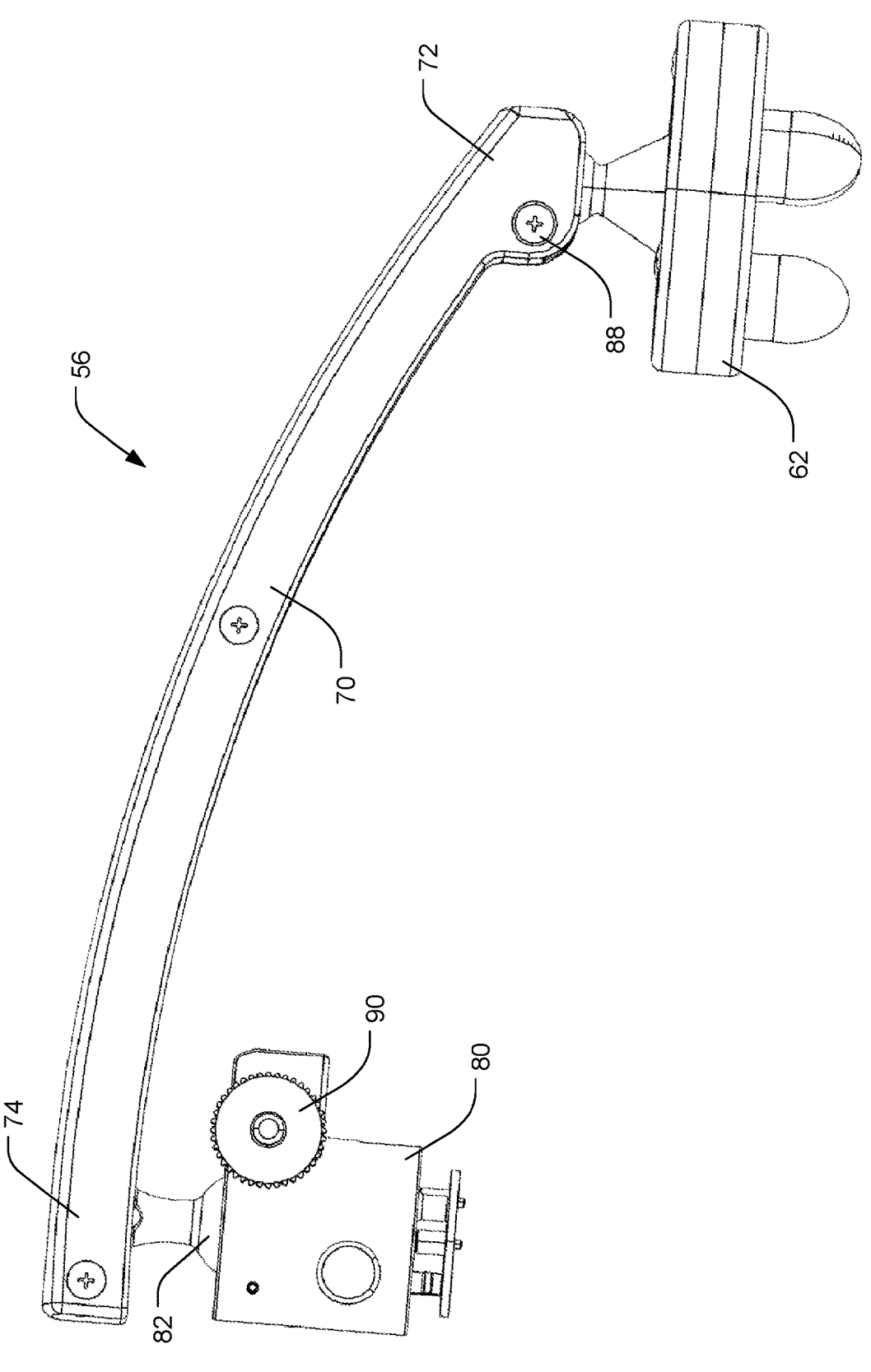
FIG. 13 shows a side view of a light arm and light pod assembly for attachment to a headpiece of a light therapy device.
Figure 14:
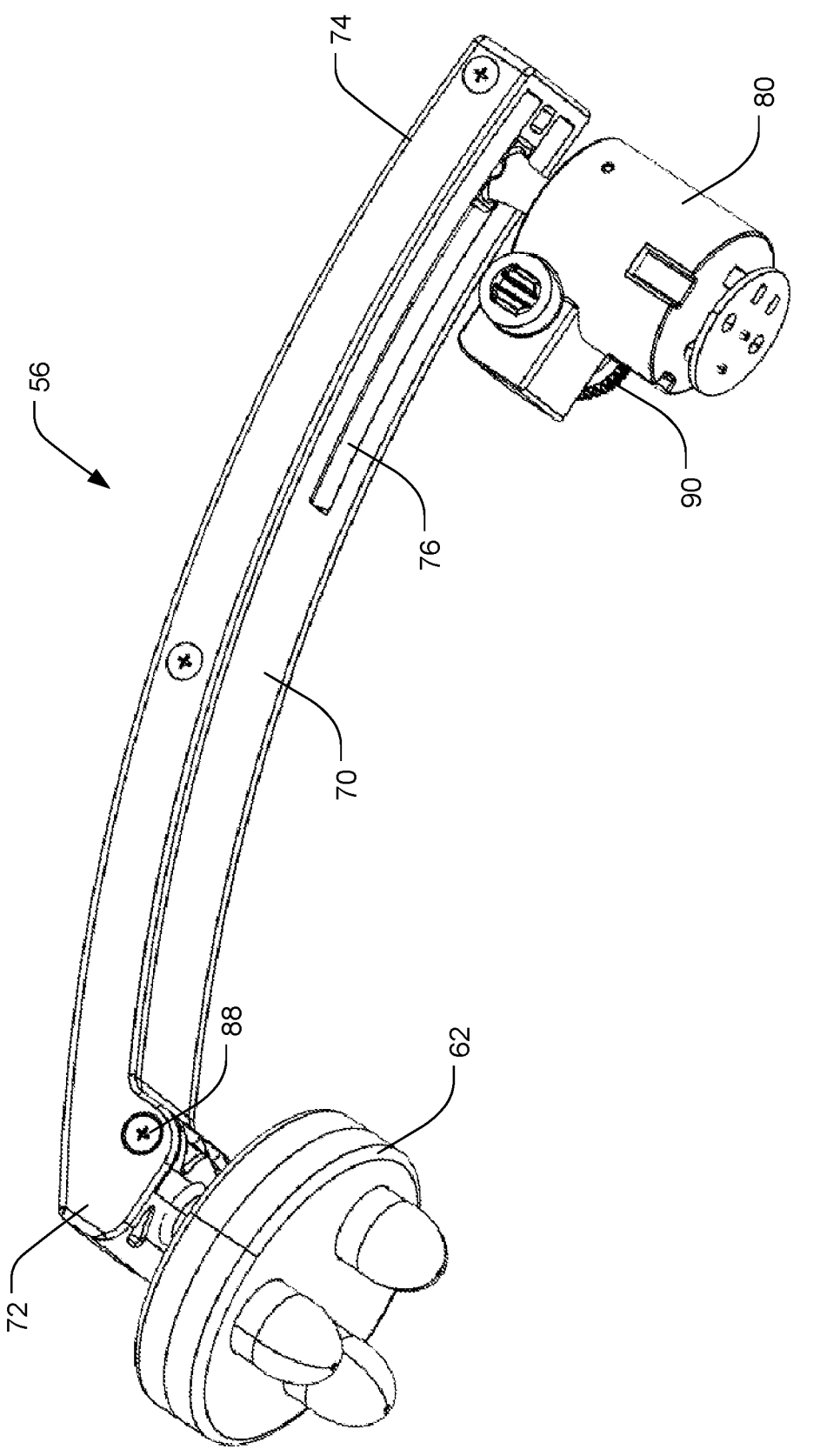
FIG. 14 shows a perspective view thereof.

The headpiece 42 of the illustrated light therapy device 40 includes attachment points for a variety of additional elements of the light therapy device 40. For example, as illustrated in FIG. 12, the central over-the-top element 46 includes one or more (four in the illustrated example) light arm attachment points 54. The light arm attachment points 54 are each shaped to provide secure reversible engagement with a light arm and light pod assembly 56. One embodiment of the light arm and light pod assembly 56 is illustrated in FIGS. 13 and 14. The light arm attachment points 54 provide both physical and electrical connection elements to engage the light arm and light pod assemblies 56. In certain embodiments of the light therapy device 40, each light arm and light pod assembly 56 is identical and each light arm attachment point 54 is identically formed (though potentially oriented differently as illustrated in FIG. 12) so as to maximize modularity and interchangeability of the elements of the light therapy device 40. In other words, in some embodiments, a single spare light arm and light pod assembly 56 can be used to replace any malfunctioning or defective light arm and light pod assembly 56 of the light therapy device 40.

Figure 18:
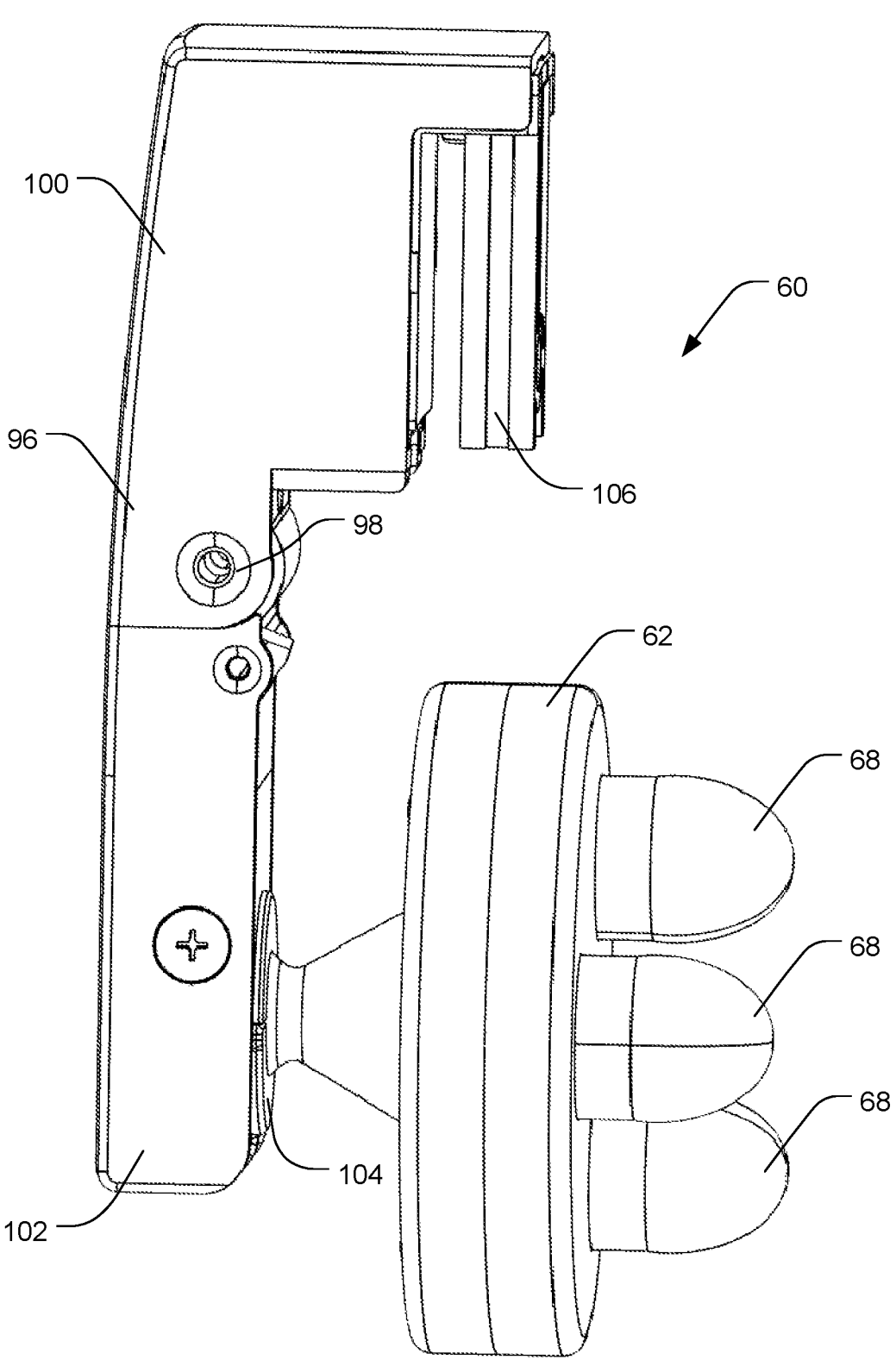
FIG. 18 shows a perspective view of a temple light support and temple light pod assembly.

Additionally, the forehead element 44 of the headpiece includes a temple attachment slot 58 on each side of the forehead element 44, corresponding to positions of the temples of the wearer. Each temple attachment slot 58 is adapted to receive and secure a temple light support and light pod assembly 60. One embodiment of the temple light support and light pod assembly 60 is illustrated in FIG. 18. The temple attachment slots 58 provide secure reversible engagement with the temple light support and light pod assemblies 60 and provide both physical and electrical connection elements to engage therewith. In certain embodiments of the light therapy device 40, each temple light support and light pod assembly 60 is identically formed so as to maximize modularity and interchangeability of the elements of the light therapy device 40. In other words, a single spare temple light support and light pod assembly 60 can be used to replace either malfunctioning or defective temple light support and light pod assembly 60 of the light therapy device 40.

Figure 17:
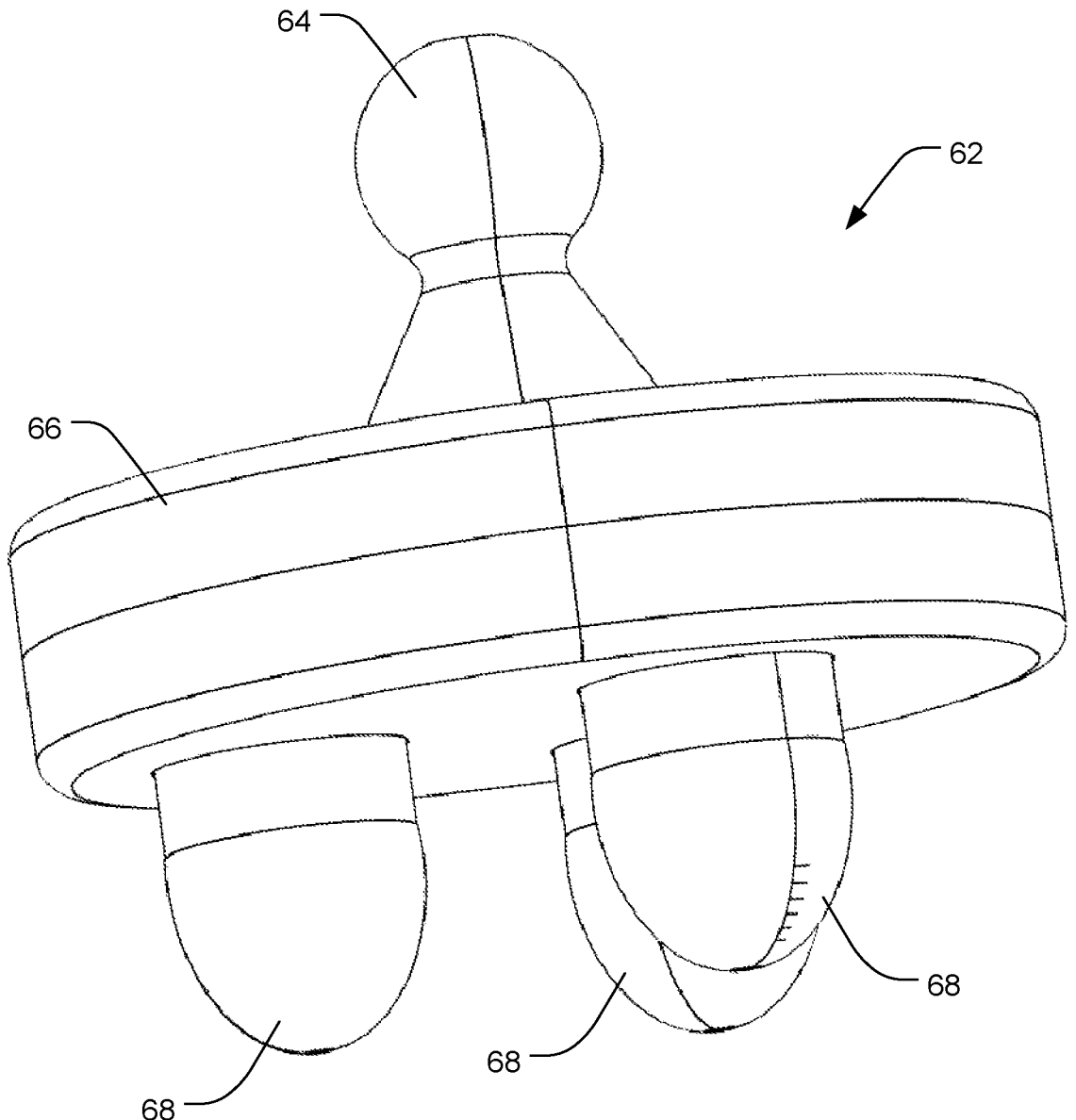
FIG. 17 shows a perspective view of one embodiment of a light pod.

In at least some embodiments of the light therapy device 40, the headpiece 42, the light arm and light pod assemblies 56 and the temple light support and light pod assemblies 60 are configured to provide maximum adjustability of placement of the respective light pods 62 of each of the various assemblies 56, 60. In accordance with the principles discussed herein of maximizing interchangeability of elements of the light therapy device 40 and simplifying manufacture thereof, the light pods 62 of each assembly 56, 60 of some embodiments are identical. One embodiment of the light pod 62 is illustrated in FIG. 17. The light pod 62 includes a ball portion 64 of a ball-and-socket joint to permit at least pivotal motion of the light pod 62 relative to its supporting element and, in some embodiments, at least some rotational motion of the light pod 62 relative to its supporting element.

As may be seen in FIG. 17, the light pod 62 includes a housing 66 and a plurality of light tubes 68, each having a bullet-shaped tip and each containing a light emitting diode (LED). In some embodiments, the light tubes 68 are internally coated to reflect the light generated by the LEDs to maximize the light energy delivered through the bullet-shaped tip of the light tubes 68. In the illustrated embodiment, each light pod 62 includes three LEDs and associated light tubes 68.

In some embodiments, the LEDs all emit identical wavelengths of light, while in other embodiments, the LEDs are selected such that different LEDs of the light pod 62 emit different wavelengths of light. The exact wavelength of light emitted by each LED may be varied as desired to achieve different treatment purposes as is known in the art, and embodiments of the light therapy device 40 are not limited to any particular wavelength of light unless specifically so stated in the claims. Nevertheless, current transcranial light therapy efforts have been primarily directed to treatment with light in the red to infrared portion of the light spectrum, so embodiments of the light pod 62 use LEDs in the red to infrared portion of the light spectrum. In particular embodiments, two of the three LEDs of the light pod 62 emit light at approximately 810 nm (within the infrared range) and the remaining LED of the light pod 62 emits light at approximately 650 nm (within the far red range of the visible spectrum).

As the purpose of the light pods 62 of the light therapy device 40 is to at least selectively deliver light transcranially as part of a light therapy treatment, it is desirable to deliver as much of the light energy generated by the LEDs as possible directly to and directed toward the skin (scalp, temples) of the wearer of the light therapy device 40. Accordingly, in at least some embodiments, an inner or outer surface of sides of the light tubes 68 is coated with a reflective material or coating such that as much as possible of the light generated by the LEDs is directed toward the rounded end of the light tube 68 as collimated light.

Similarly, the pivotal movement of the light pods 62 by use of the ball-and-socket joint connecting the light pods 62 to their respective support elements allows each light pod 62 to pivot until each of the three tips of the light tubes 68 directly contacts the skin, thus minimizing the distance the light has to travel before entering the wearer's skin (and then passing through the cranium). As the intensity of the delivered light is maximized by minimizing the distance between the tip of each light tube 68 and the wearer's skin, contacting the tip of all of the light tubes 68 to the skin increases the effectiveness of the light treatment. Accordingly, the ball-and-socket joint with which each light pod 62 is attached to the light therapy device 40 maximizes the effectiveness of embodiments of the light therapy device 40 with such joints, as it allows all light tubes 68 to be positioned in contact with the skin.

Figure 15:
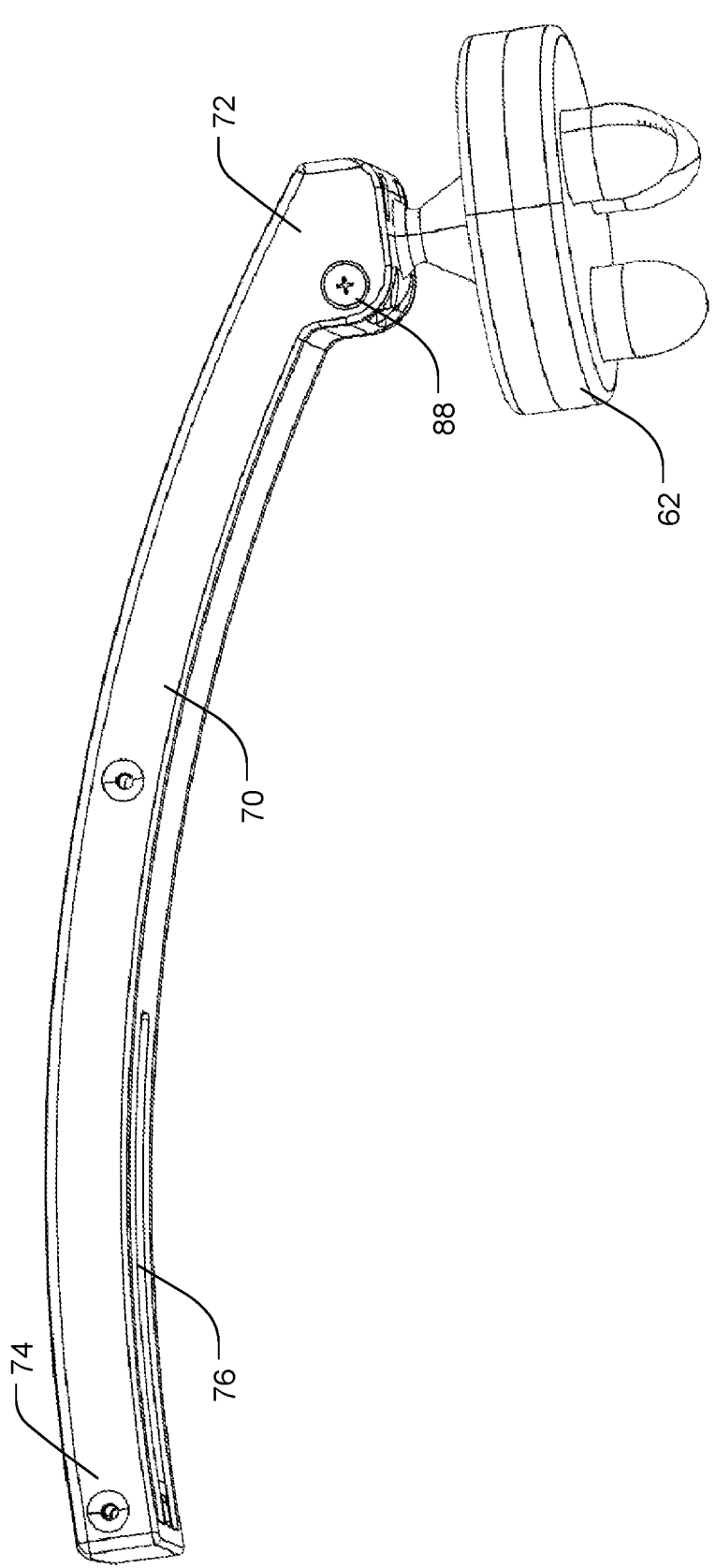
FIG. 15 shows a perspective view of a light arm and light pod assembly without a headpiece-light arm joint element attached thereto.

Other features of embodiments of the light arm and light pod assemblies 56 and of the temple light support and light pod assemblies 60 similarly maximize the proximity of the LEDs (and/or bullet-shaped tip of the light tubes 68) to the wearer's skin. Such features of some embodiments of the light arm and light pod assemblies 56 and of the temple light support and light pod assemblies 60 also serve to maximize flexibility of the location of placement of the various light pods 62 for fitment or varying treatment or therapy purposes. For example, in embodiments of the light arm and light pod assemblies 56 (see FIGS. 13 and 14), the light arm and light pod assemblies 56 are formed with a light arm 70 with a distal end 72 (housing the socket portion of the ball-and-socket joint with the light pod 62) and a proximal end 74. FIG. 15 shows a view of an embodiment of the light arm 70 attached to its light pod 62. As may be seen in FIG. 15, the proximal end 74 of the light arm 70 includes an engagement slot 76.

Figure 16:
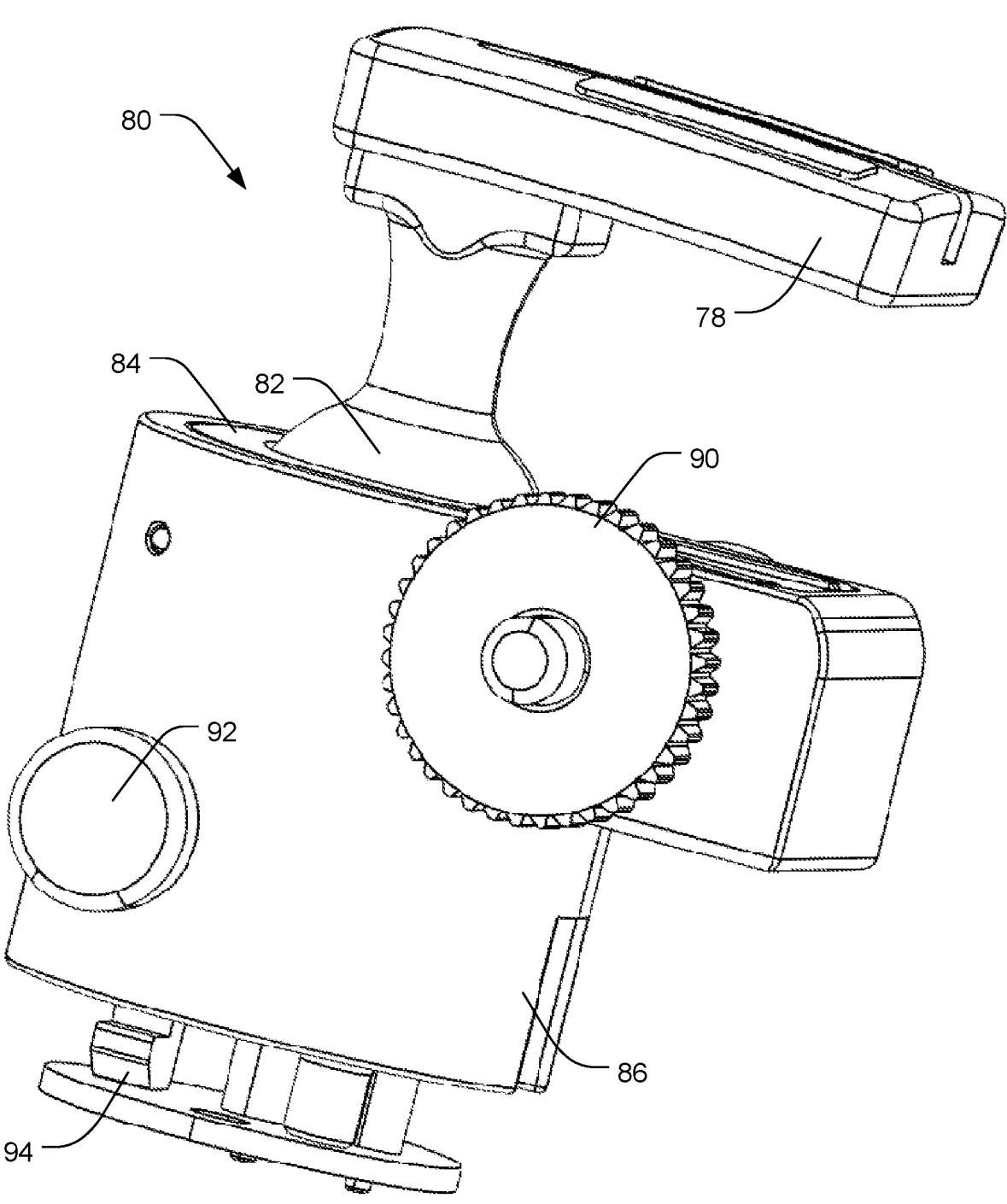
FIG. 16 shows a perspective view of a headpiece-light arm joint element.

The engagement slot 76 is adapted to engage with a pin portion 78 of a headpiece-light arm joint assembly 80. One embodiment of the headpiece-light arm joint assembly 80 is illustrated in FIG. 16. As may be seen in FIG. 16, the pin portion 78 of the headpiece-light arm joint assembly 80 includes a ball portion 82 of a ball-and-socket joint that is engaged with a socket portion 84 of the ball-and-socket joint that is located on a headpiece side 86 of the headpiece-light arm joint assembly 80. The pin-and-slot engagement of the pin portion 78 in the engagement slot 76 allows the light arm 70 to slide relative to the headpiece-light arm joint assembly 80, thereby allowing the light pod 62 to be placed closer to or farther from the central over-the-top element 46. This permits the light pod 62 to be properly placed at different locations for different treatment or therapy modalities or at similar locations of differently sized or shaped heads and/or heads having different hair coverage for similar treatment or therapy modalities on different wearers.

Meanwhile, the ball-and-socket joint between the pin portion 78 and the headpiece side 86 of the headpiece-light arm joint assembly 80 allows for at least pivotal motion of the light arm 70 relative to the headpiece 42 and, in at least some embodiments, allows for at least some rotational motion of the light arm 70 around the headpiece-light arm joint assembly 80. The pivotal motion of the light arm 70 facilitates movement of the light pod 62 at the distal end 72 of the light arm toward or away from the head of the wearer, such that the light pod 62 can be placed with the bullet-shaped tip of the light tube 68 in direct contact with the wearer's skin. (Such contact is provided in conjunction with the at least pivotal movement of the light pod 62 relative to the light arm 70 at the light pod's ball-and-socket joint which allows direct skin contact of all three bullet-shaped tips of the light tubes 68 at the point of contact of the light pod 62, in what is facilitated by what may be termed dual gimbal movement provided by the two ball-and-socket joints in conjunction.) Accordingly, the pivotal motion provided by the headpiece-light arm joint assembly 80 maximizes the treatment efficacy of each light pod 62 of the light therapy device 40.

Additionally, as may be appreciated, the at least some rotational motion of the light arm 70 around the headpiece-light arm joint assembly 80 provided by some embodiments of the headpiece-light arm joint assembly 80 further facilitates desirable variation of placement or location of the light pods 62. Accordingly, such rotational movement facilitates either different placement of the light pods 62 for different treatment or therapy modalities, or different placement of the light pods 62 for similar treatment or therapy modalities on different wearers having differently sized or shaped heads and/or heads with different hair coverage.

Electrical connections are provided between the headpiece and the headpiece-light arm joint assembly 80 and between the headpiece-light arm joint assembly 80 and the light arm 70. Such electrical connections are completed as the various components are engaged together as is known in the art. In some embodiments, similar electrical connections are provided between the light arm 70 and the light pod 62 and are similarly completed as the light pod 62 is engaged together with the light arm 70. Alternatively, in other embodiments, electrical connections between the engagement slot 76 and the light pod 62 are provided as more-or-less permanent wires, whereby the light pod 62 is not intended for user removal from the light arm 70.

The ball-and-socket joints of the connection between the light pod 62 and the light arm 70 and of the headpiece-light arm joint assembly 80 are optionally provided with tightening features in some embodiments. For example, the distal end 72 of the light arm 70 of some embodiments is provided with one or more tightening screws 88. In most embodiments, adjustment of the tightening screw 88 or tightening screws 88 will only occasionally be necessary. As another example, the headpiece-light arm joint assembly 80 of some embodiments is provided with a thumbscrew 90, allowing for ready tightening or loosening of the ball-and-socket joint at the headpiece-light arm joint assembly 80. As such adjustment of some embodiments may be more-common, the thumb screw 90 provides easier adjustment of this joint.

The headpiece-light arm joint assembly 80 of some embodiments further includes a release button 92 and an engagement tab 94 operated by the release button 92. The engagement tab 94 engages a corresponding structure of the light arm attachment point 54. Accordingly, the engagement tab 94 secures the light arm and light pod assembly 56 to the headpiece 42 until the user desires to separate them by pressing the release button 92 to release the light arm and light pod assembly 56 from the headpiece 42. In some embodiments, release of the light arm and light pod assembly 56 from the headpiece 42 requires both pressing of the release button and twisting the light arm and light pod assembly 56 in the light arm attachment point 54 for increased security of engagement against accidental release.

Corresponding features of embodiments of the temple light support and light pod assemblies 60 similarly maximize the delivery of light energy to the wearer's skin, and also serve to maximize flexibility of the location of placement of the temple light pods 62 for fitment or varying treatment or therapy purposes. The temple attachment slots 58 are formed as slots, thereby allowing translation of the temple light support and light pod assemblies 60 forward or backward on the forehead element 44, thereby allowing variation in forward-backward placement of the temple light support and light pod assemblies 60 on the wearer's temples. The temple light support and light pod assemblies 60 each include a temple light support 96 with a support hinged connection 98 connecting an upper portion 100 to a bottom portion 102.

In some embodiments, the LEDs of the temple light support and light pod assemblies 60 are housed in light tubes 68, similar to or identical to the manner in which the LEDs are housed in light tubes 68 in the light pods 62 of the light arm and light pod assembly 56, for similar purposes. In some embodiments, the support hinged connection 98 is spring loaded to bias the light pod 62 of the temple light support and light pod assembly 60 toward the temple of the wearer, thereby ensuring contact between the bullet-shaped tip of the light tubes 68 of the light pod 62 and the wearer's skin. In other embodiments, the light pod 62 of the temple light support and light pod assembly 60 is otherwise biased toward the temple of the wearer. The bottom portion 102 includes a socket portion 104 of a ball-and-socket joint between the light pod 62 and the temple light support 96. This provides pivotal motion of the light pod 62 relative to the temple light support 96, ensuring that all three of the bullet-shaped tips of the light tubes 68 are able to contact the skin, and, in at least some embodiments, some rotational movement of the light pod 62. The top portion 104 of the temple light support 96 includes an engaging tab 106 adapted to slidingly engage with the temple attachment slots 58 and, in some embodiments, provide electrical connections between the temple light support and light pod assembly 60 and the headpiece 42.

Figure 7:
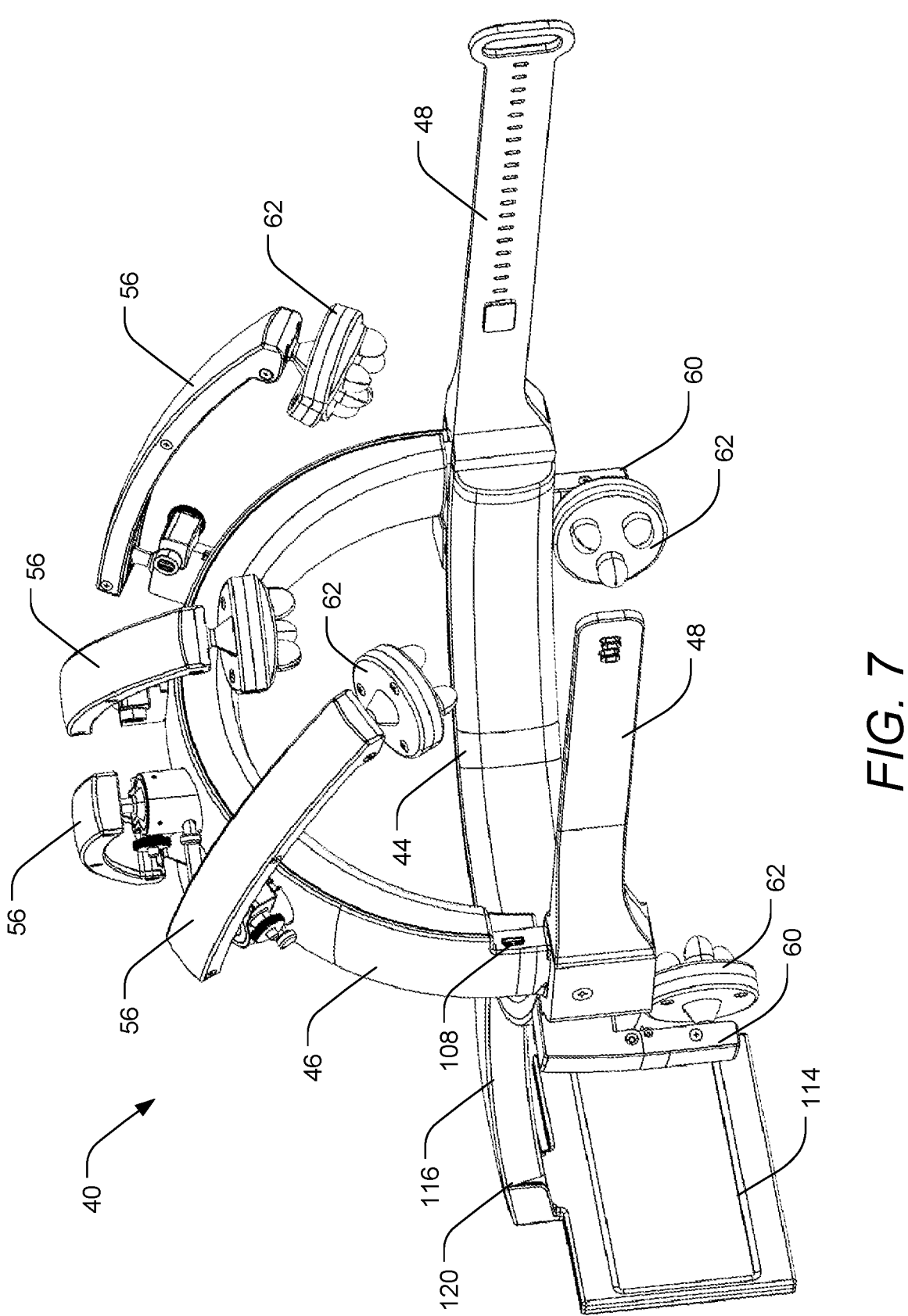
FIG. 7 shows another perspective view thereof.
Figure 8:
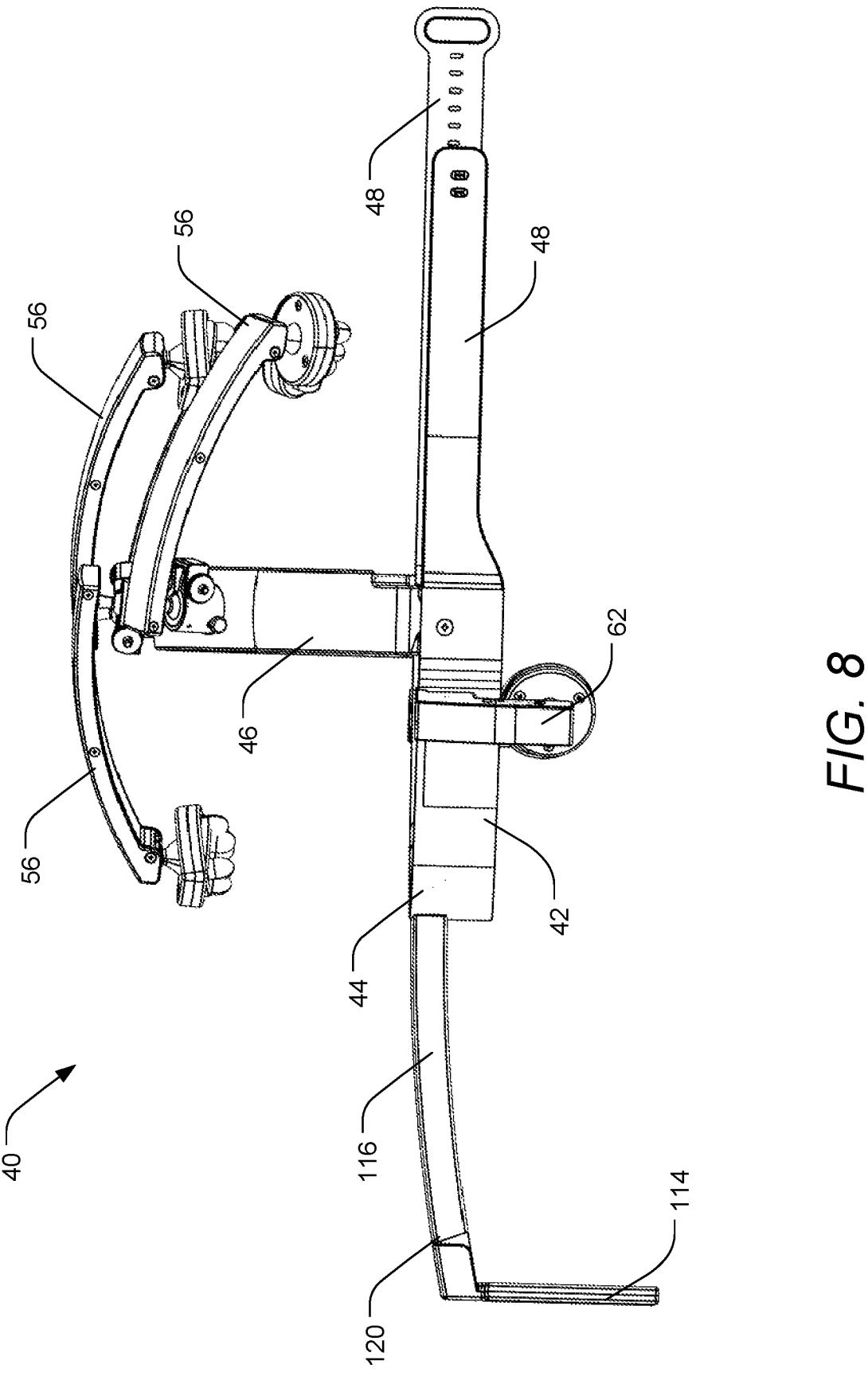
FIG. 8 shows a left side view thereof.
Figure 9:
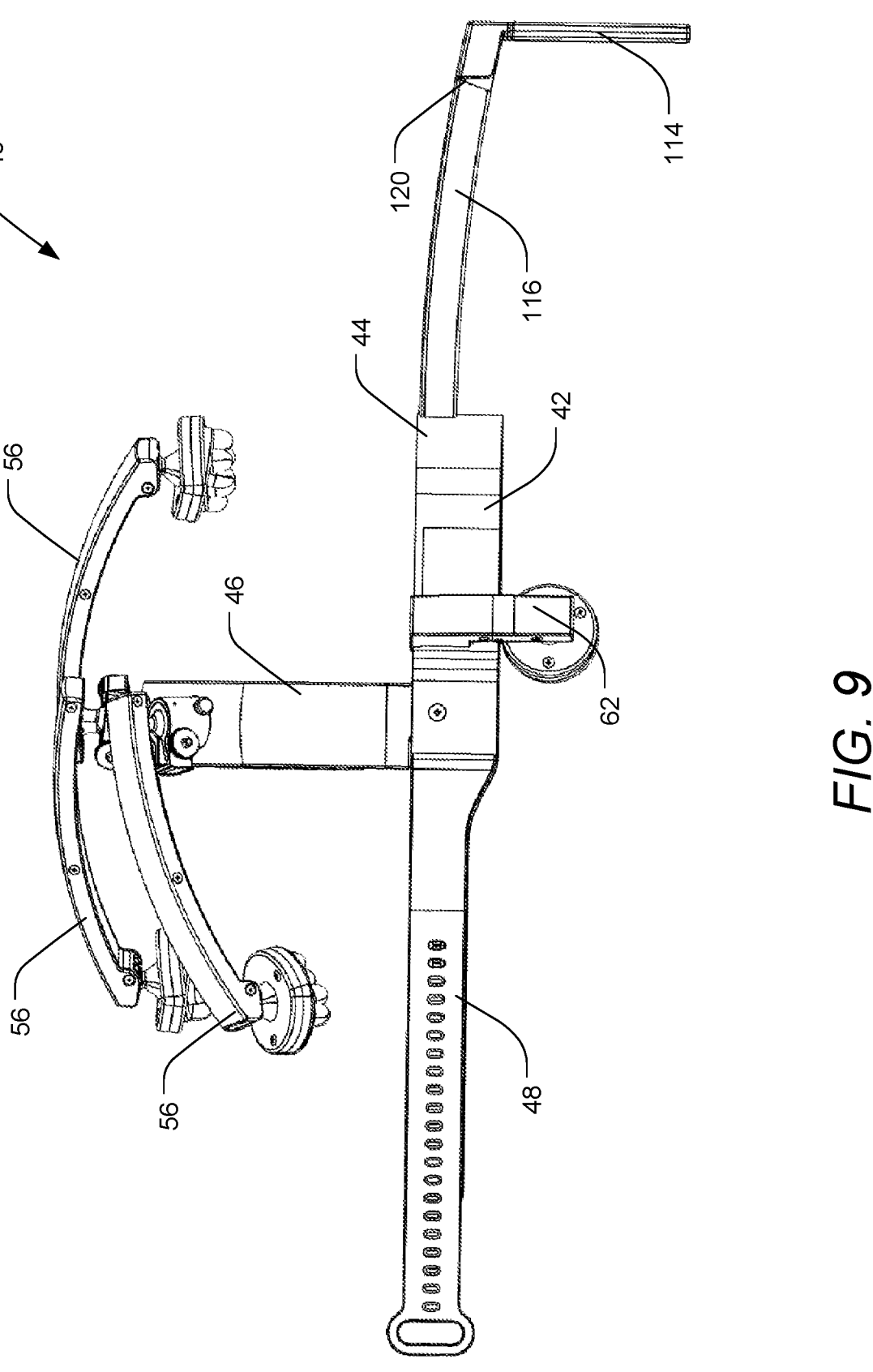
FIG. 9 shows a right side view thereof.
Figure 10:
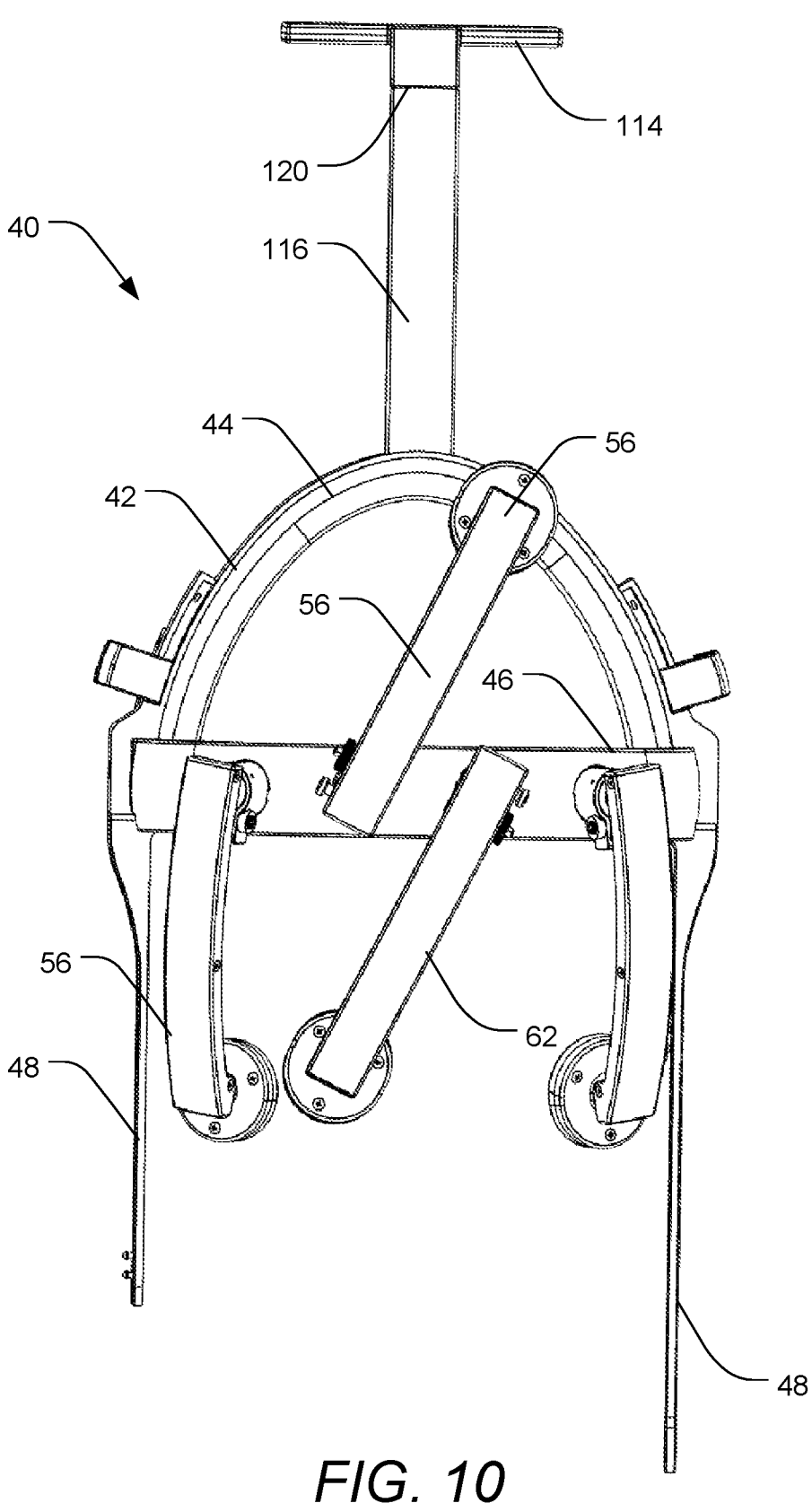
FIG. 10 shows a top view thereof.
Figure 11:
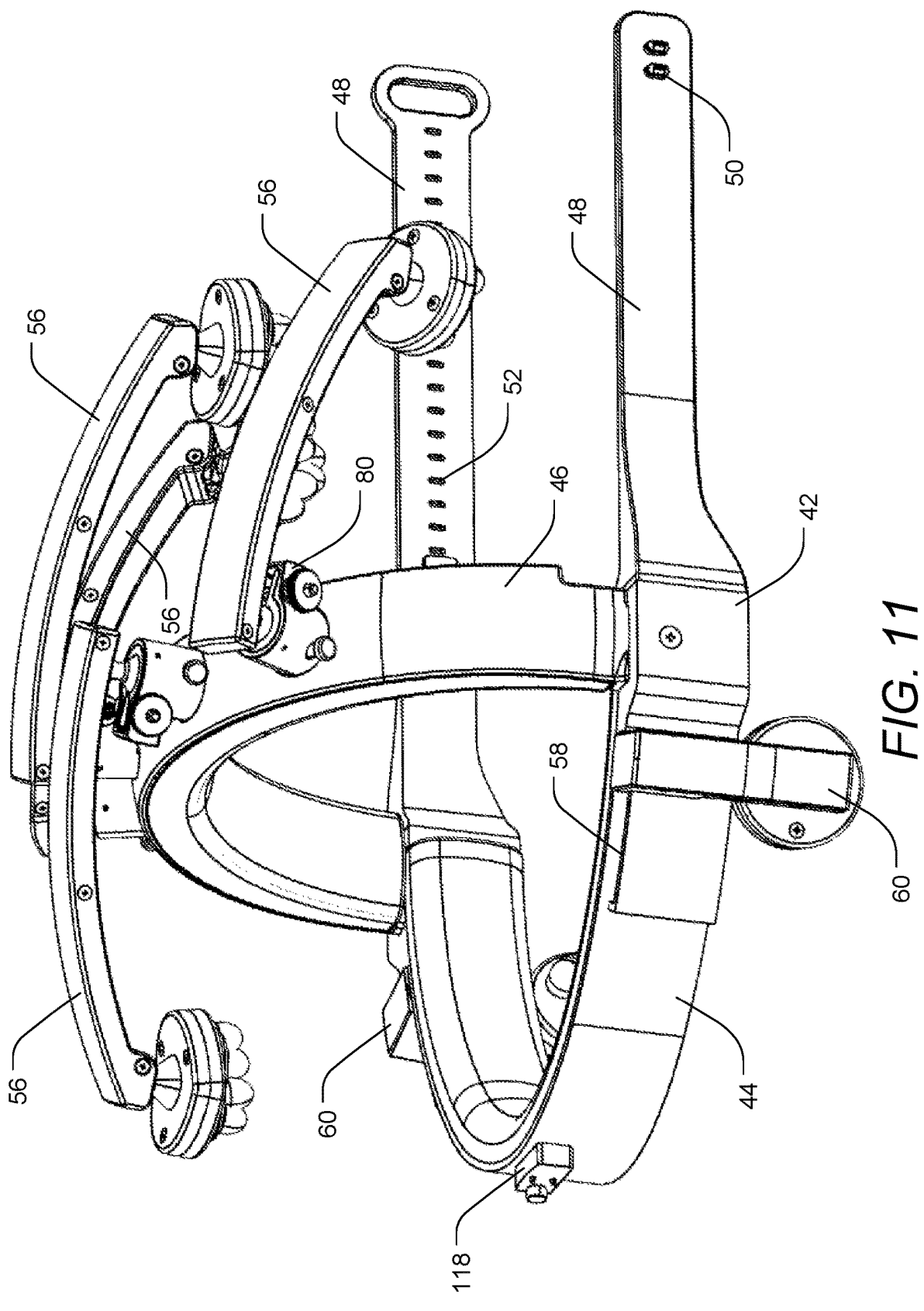
FIG. 11 shows a perspective view of a light therapy device without a visible light panel or control box attached thereto.

When the headpiece 42 is assembled with all of its assemblies 56, 60, it assumes the configuration shown in FIG. 11. The headpiece 42 includes a control port 108 (best shown in FIG. 7) enabling wired connection of a control box 110 or other controller (as seen in FIGS. 2-3) to the headpiece 42. The headpiece 42 includes wires running to the various attachment points for assemblies 56, 60 (e.g., within the forehead element 44 and the central over-the-top element 46). The control port 108 includes sufficient wire connections to enable independent and discrete control of individual light elements of the light therapy device 40. Such independent and discrete control of some embodiments is by individual light pod 62. In other embodiments, such independent and discrete control is by individual LED. In other embodiments, such independent and discrete control is by individual LED type (e.g., by all infrared LEDs as opposed to all red LEDs). In still other embodiments, such independent and discrete control is by a combination of LED type and light pod 62 (e.g., all infrared LEDs of selected light pods 62 separately from red LEDs of the selected light pods 62). Accordingly, embodiments of the light therapy device 42 permit a wide variety of independent control of individual light elements.

In some embodiments of the light therapy device 40, the control box 110 includes a power supply (e.g., one or more batteries) or is operatively connected to a power source. In such embodiments, power is then delivered by the wired connection to the headpiece 42 and on to the light pods 62, such as by a cable 112 (having an appropriate number of separate insulated strands) extending between the control box 110 or other controller and the headpiece 42. In other embodiments, power is supplied directly to the headpiece 42 (such as by one or more batteries or by a separate power connection directly to the headpiece), and only control is provided by the cable 112 extending between the control box 110 or other controller and the headpiece 42. In still other embodiments, the control box 110 or other controller is only wirelessly connected to the headpiece 42 using any appropriate type of wireless connection (e.g., by Bluetooth, WiFi (IEEE 802.11x), proprietary protocol, or the like). In some such embodiments, the headpiece 42 is powered by a self-contained power source incorporated into the headpiece (e.g., one or more batteries), and in other such embodiments, the headpiece 42 is connected to an external power source either by one or more wires or wirelessly (e.g., inductive powering).

In some embodiments of the light therapy device 40, the control box 110 or other controller is at least intermittently operatively connected to a separate computing device and is capable of conveying treatment or therapy data to the separate computing device and/or is capable of receiving treatment or therapy instructions from the separate computing device. In some embodiments, the connection to the separate computing device is a wired connection, and in other embodiments, the connection to the separate computing device is a wireless connection. In other embodiments of the light therapy device 40, the control box 110 is replaced by a computing device as discussed above with respect to FIG. 1, and the computing device provides signals and/or power to the headpiece (or the various elements thereof) to achieve the desired therapy or treatment.

In some embodiments of the light therapy device 40, control of which light pods 62 deliver light to the subject may be achieved in a variety of manners. As discussed previously, such control may be achieved by separate control through the control box 110 or other controller (including by the separate computing device, if used). In some embodiments, control of which light pods 62 deliver therapy or treatment to the subject may be achieved, at least in part, by removing one or more light arm and light pod assemblies 56 or by removing one or both of the temple light support and light pod assemblies 60 from the headpiece 42. In some embodiments, control of which light pods 62 deliver therapy or treatment to the subject may be achieved, at least in part, by adjusting the placement one or more of the light arm and light pod assemblies 56 such that the LEDs and/or the bullet-shaped tips of the light tubes 68 are distanced from the skin of the subject. Between light fall-off that occurs with distance and any intervening scalp hair, placing distance between a light pod 62 and the skin effectively reduces or eliminates treatment or therapy from that light pod 62. In some embodiments, control of which light pods 62 deliver therapy or treatment may occur using any combination of any of these mechanisms or methods.

Some embodiments of the light therapy device 40 provide visible light therapy delivered ocularly to the subject. Such visible light therapy is provided simultaneously with the transcranial light therapy provided by the one or more light pods 62 in some embodiments. In some embodiments, such visible light therapy is provided consecutively with the transcranial light therapy. In some embodiments, the visible light therapy is provided independently from any transcranial light therapy or may be provided in the absence of any transcranial light therapy. Accordingly, the presence or use of visible light therapy using embodiments of the light therapy device 40 is not limited by any use (or not) of the transcranial light therapy or by the presence or absence of any assemblies 56, 60 with their associated light pods 62.

The visible light therapy of the light therapy device 40 is provided by a visible light panel 114 that is selectively attached to the headpiece 42 by a light bar 116 that attaches to a light bar attachment point 118 (see FIGS. 11 and 12)

located on the forehead element 44 (centrally located on a forward surface of the forehead element 44 in the illustrated embodiments, but not necessarily so located in all embodiments). The visible light panel 114 includes one or more LEDs that provide soft, cool, white light (e.g., in the range of wavelengths of approximately 380-750 nm) to the eyes of the subject. When the visible light panel 114 is not in use, it can be flipped up at a visible light panel-light bar joint 120 that provides a hinged connection between the visible light panel 114 and the light bar 116. Electrical power is provided to the light panel 114 through the light bar attachment point 118 similar to the manner in which electrical power is provided to the assemblies 56, 60 discussed previously.

The visible light panel 114 of certain embodiments of the light therapy device is independently controlled using methods or mechanisms similar to those discussed above. By way of example, the visible light panel 114 can be independently controlled by any one or more of a separate control on the control box 110 or other controller, detachment/attachment of the visible light panel 114 and light bar 116 from/to the light bar attachment point 118, flipping up of the visible light panel 114 at the visible light panel-light bar joint 120, and the like.

Some embodiments of the light therapy device 40 provide intranasal light therapy delivered to a nasal canal of the subject. Such intranasal light therapy is provided simultaneously with the transcranial light therapy provided by the one or more light pods 62 and/or the visible light therapy provided by the visible light panel 114 in some embodiments. In some embodiments, such intranasal light therapy is provided consecutively with the transcranial light therapy and/or the visible light therapy. In some embodiments, the intranasal light therapy is provided independently from any transcranial light therapy and/or visible light therapy or may be provided in the absence of any transcranial light therapy or visible light therapy. Accordingly, the presence or use of intranasal light therapy using embodiments of the light therapy device 40 is not limited by any use (or not) of the transcranial light therapy or visible light therapy or by the presence or absence of any assemblies 56, 60 with their associated light pods 62 or by the presence or absence of the visible light panel 114.

Figure 21:
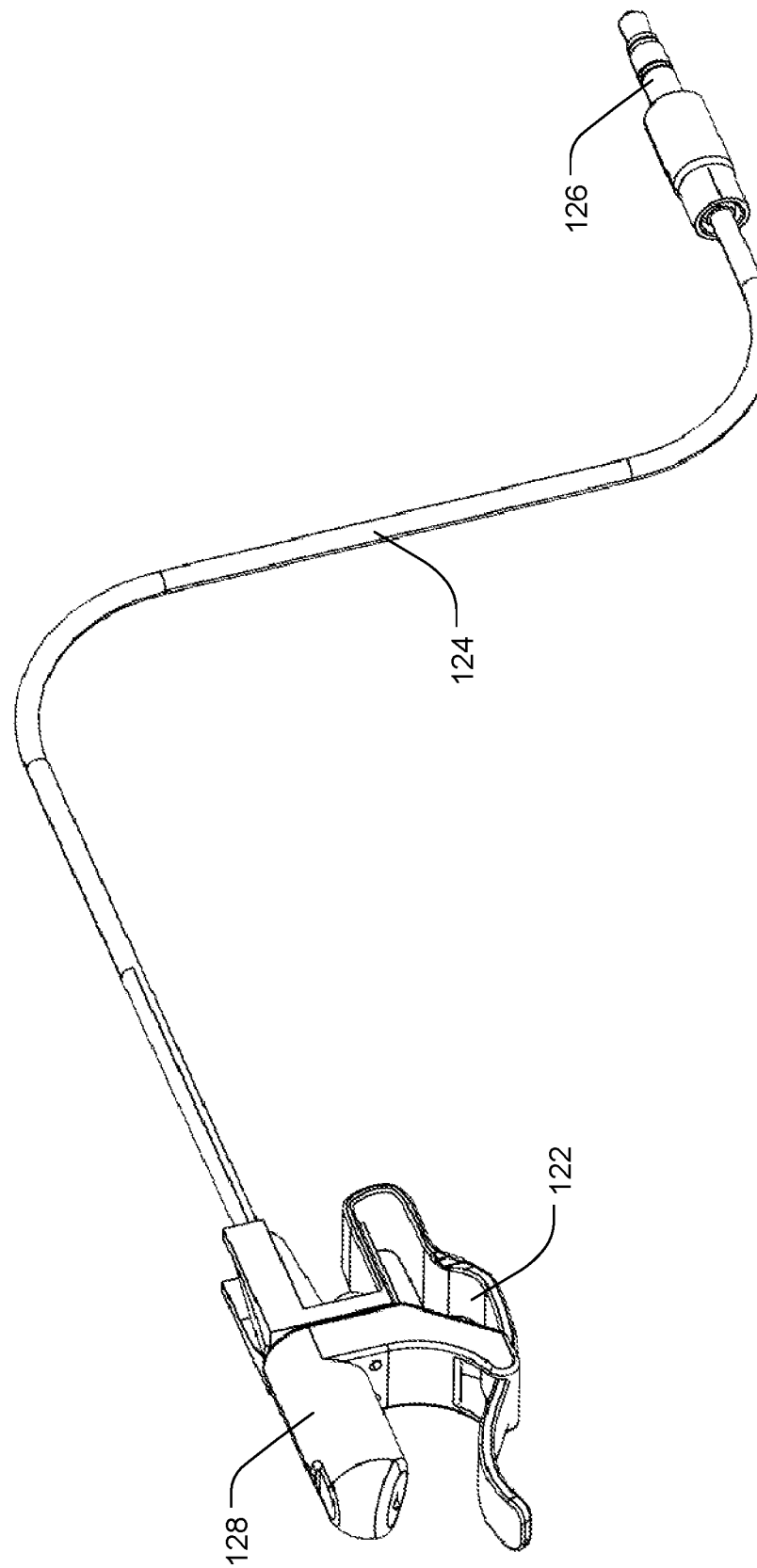
FIG. 21 shows a perspective view of one embodiment of a nasal clip for selective connection to and use with embodiments of a light therapy device.

The intranasal light therapy of the light therapy device 40 is provided by a nasal clip 122 that is selectively attached to any desirable location on the light therapy device 40 by a nasal cable 124 of any desirable length (see FIG. 21). In some embodiments, the nasal cable 124 attaches to the headpiece 42, and in other embodiments, as illustrated in FIGS. 2 and 3, the nasal cable 124 connects to the control box 110 or other controller. The connection of certain embodiments is accomplished using a plug 126 of any desirable configuration. The nasal clip 122 includes one or more nasal LEDs, which in some embodiments are contained in a nasal light tube 128 optionally having a bullet-shaped tip as discussed with LEDs and light tubes previously, delivering light at one or more desirable frequencies (such as at one or both of 810 nm or 650 nm, for example). The one or more nasal light tubes 128 may include a coating or reflective light tube as described previously to obtain collimated light delivery intranasally from the LED or LEDs.

The intranasal light therapy can be controlled independently from the therapy provided by the other light elements. In some embodiments, the independent control is achieved by a control on the control box 110 or other controller. In some embodiments, the independent control is achieved by not placing the nasal clip 122 in the nostril of the subject. In some embodiments, the independent control is achieved by connecting (or not) the plug 126 to its corresponding receptacle. Accordingly, any method or mechanism may be used to independently control the intranasal light therapy.

Figure 19:
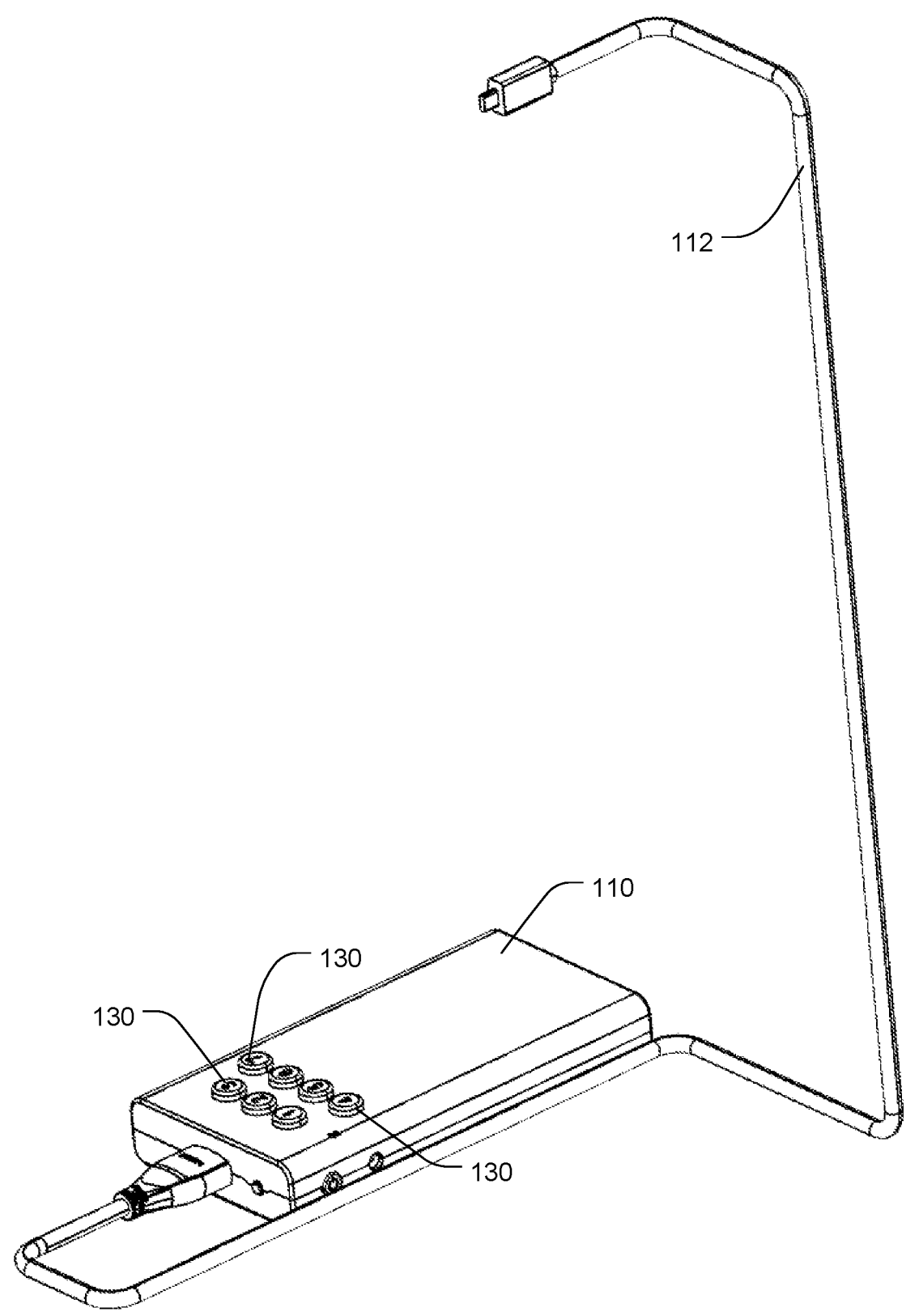
FIG. 19 shows a perspective view of one embodiment of a control box or controller for a light therapy device with one embodiment of a connecting cable for connection to a headpiece of a light therapy device.
Figure 20:
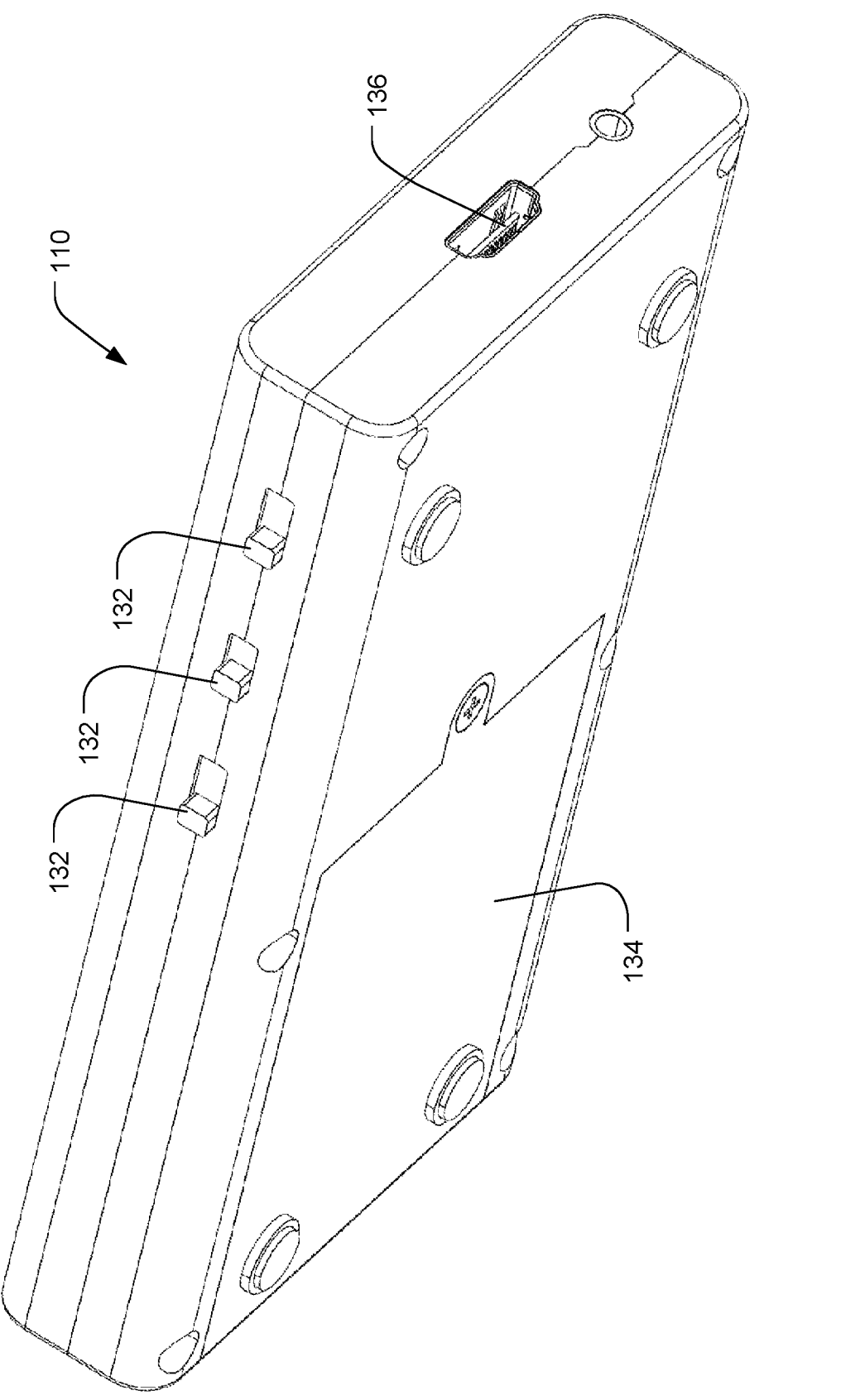
FIG. 20 shows a perspective view of the control box or controller of FIG. 19.

As described previously, in some embodiments, the control box 110 or other controller allows for asynchronous control of any or all of the light-delivery elements of the light therapy device 40. FIGS. 19 and 20 illustrate manners in which one embodiment of the control box 110 achieves such control as well as other control aspects of the light therapy or light treatment provided by the light therapy device 40. The control box 110 includes a front surface that has a plurality of activation buttons 130. Each activation button 130 activates one of the light pods 62 or the visible light panel 114, or the one or more nasal LEDs of the nasal clip 112. In the illustrated embodiment, there are seven activation buttons 130 corresponding to the six light pods 62 and one visible light panel 114 (control of the one or more nasal LEDs is achieved by another of the methods discussed previously). In other embodiments, another number of activation buttons is present.

In one example of use, the user selects the number of activation buttons to press to select light elements to activate, then activates another control to begin therapy or treatment, upon which the corresponding light elements are activated. In another example of use, the user activates a control to begin therapy, then presses the desired activation buttons whenever desired to activate the corresponding light elements. Any desirable activation process may be used with the varying embodiments of the control box 110 or other controller.

The view of the control box 110 shown in FIG. 20 illustrates a number of selection switches 132 serving to control aspects of the light therapy or treatment. By way of example, one selection switch 132 controls an operating frequency of the light elements switching on and off (e.g., at a duty cycle of between approximately 30% to approximately 70%, or approximately 50% in some embodiments), such as selecting between 10 Hz and 40 Hz. The specific frequencies provided by the selection switch 132 may be selected to provide desired treatment modalities, and can be of more than two options. As another example, a second of the selection switches 132 serves to control a power density of the light applied by the various light pods 62 (e.g., approximately 25 mW/cm2, approximately 40 mW/cm2, and approximately 100 mW/cm2). The specific power densities provided by the selection switch 132 may be selected to provide desired treatment modalities, and can be of fewer than three options or more than three options, as desired. As another example, a third of the selection switches 132 serves to control a treatment duration for which the light pods 62 operate (e.g., approximately 5 minutes, approximately 20 minutes, approximately 30 minutes, and approximately 50 minutes). The specific treatment durations provided by the selection switch 132 may be selected to provide desired therapy goals, and can be of fewer than four options or more than four options. Accordingly, the specific selection switch options discussed herein are not considered to be the only options provided by various embodiments of the light therapy device 40.

One of ordinary skill in the art will readily recognize that controls other than those illustrated and discussed with respect to the specific control box 110 of FIGS. 19 and 20 may be used to provide control of the various light delivery elements of the various embodiments of the light therapy device 40. The control box 110 of certain embodiments also includes various lights or other indicators to indicate selected treatment or therapy modalities or options, thereby communicating with the user and aiding the user in selecting appropriate selections. FIG. 20 also illustrates a battery compartment 134 illustrating one manner in which the light therapy device 40 may receive power. As shown in FIG. 20, the control box also includes a control port 136 adapted to receive connection with the cable 110.

The various elements of the light therapy device 40 may be formed from any of a variety of appropriate materials selected to provide desirable physical characteristics while providing appropriate durability to permit use during a planned lifetime of the light therapy device. One of ordinary skill in the art will readily appreciate appropriate materials for the various elements (such as appropriate plastics such as polycarbonate, lightweight metals, and the like), and accordingly embodiments of the light therapy device 40 are not limited to construction with any particular material.

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by Letters Patent is:

1. A light therapy device, comprising:
a headpiece comprising a top piece oriented in a first orientation and a strap piece oriented in a second orientation pivotally connected to the top piece;
four light arms, each light arm comprising a proximal end and a distal end;
four headpiece-light arm joints, each headpiece-light arm joint being disposed proximate the proximal end of a respective one of the four light arms and connecting the headpiece and the corresponding light arm in such a way that provides rotational and pivotal motion of the corresponding light arm relative to the headpiece;
two temple light supports;
two headpiece-temple light support joints, each headpiece-temple light support joint connecting a respective one of the two temple light supports to the headpiece;
four light arm-light pod joints;
two temple light support-light pod joints;
six light pods, wherein each light arm-light pod joint connects one of four of the light pods to a corresponding one of the four light arms, and wherein each temple light support-light pod joint connects one of two of the light pods to a corresponding one of the two temple light supports; and
a flip-up visible light panel, wherein the visible light panel comprises:
a light bar having a proximal end and a distal end, wherein the proximal end of the light bar is selectively and removably connected to a front of the headpiece; and
a visible light panel-light bar joint, wherein the visible light panel-light bar joint is disposed at the distal end of the light bar and connects the visible light panel and the light bar in such a way that provides hinged motion of the visible light panel relative to the light bar.

2. The device of claim 1, wherein the headpiece is adapted to rest on a human head.

3. The device of claim 1, wherein each light arm is selectively connected to the light arm joint in such a way that provides sliding translational motion of the light arm relative to the headpiece.

4. The device of claim 3, wherein a pin slot joint selectively connects the light arm and the light arm joint to provide the sliding translational motion of the light arm relative to the headpiece.

5. The device of claim 1, wherein each of the headpiece-light arm joints comprises a ball and socket joint.

6. The device of claim 1, wherein each light arm-light pod joints comprises a ball and socket joint providing at least pivotal motion of the light pod relative to the light arm.

7. The device of claim 1, wherein each of the light pods comprises a plurality of light-emitting diodes ("LEDs").

8. The device of claim 7, wherein each of the light pods comprises three LEDs.

9. The device of claim 7, wherein the LEDs are each enclosed within a light tube having a bullet-shaped lens covering that provides direct scalp contact, and wherein the light tubes are internally coated to reflect light from the LEDS and target light delivery through the tip of each light tube or lens covering.

10. The device of claim 1, wherein the headpiece-temple light support joint comprises a clip.

11. The device of claim 1, wherein the temple light support-light pod joint comprises a ball and socket joint.

\* \* \* \* \*